United States Patent
Jin et al.

(10) Patent No.: US 10,131,574 B2
(45) Date of Patent: Nov. 20, 2018

(54) ANTIMICROBIAL GLASS ARTICLES AND METHODS OF MAKING AND USING SAME

(71) Applicant: CORNING INCORPORATED, Corning, NY (US)

(72) Inventors: Yuhui Jin, Painted Post, NY (US); Charlotte Diane Milia, Corning, NY (US); Christine Coulter Wolcott, Horseheads, NY (US)

(73) Assignee: CORNING INCORPORATED, Corning, NY (US)

( * ) Notice: Subject to any disclaimer, the term of this patent is extended or adjusted under 35 U.S.C. 154(b) by 370 days.

(21) Appl. No.: 14/306,317

(22) Filed: Jun. 17, 2014

(65) Prior Publication Data
US 2014/0370303 A1 Dec. 18, 2014

Related U.S. Application Data

(60) Provisional application No. 61/835,959, filed on Jun. 17, 2013.

(51) Int. Cl.
| C03C 21/00 | (2006.01) |
| C03C 23/00 | (2006.01) |
| A01N 59/16 | (2006.01) |

(52) U.S. Cl.
CPC ............ C03C 21/005 (2013.01); A01N 59/16 (2013.01); C03C 21/002 (2013.01); C03C 23/0075 (2013.01); C03C 2204/02 (2013.01); Y10T 428/315 (2015.01)

(58) Field of Classification Search
CPC .......................... C03C 21/005; C03C 23/0075
See application file for complete search history.

(56) References Cited

U.S. PATENT DOCUMENTS

| 1,494,147 | A | * | 5/1924 | Braun | .................... | C11D 7/265 |
| | | | | | | 510/182 |
| 2,981,642 | A | * | 4/1961 | Danaczko, Jr. | ...... | H01C 17/281 |
| | | | | | | 134/2 |

(Continued)

FOREIGN PATENT DOCUMENTS

| AU | 2002358123 A1 | 6/2003 | ............... A61K 8/00 |
| AU | 2002358123 A8 | 6/2003 | ............... A61K 8/00 |

(Continued)

OTHER PUBLICATIONS http://cell-phones.toptenreviews.com/smartphones/terrifying-germs-that-live-on-your-smartphone.html.

(Continued)

*Primary Examiner* — Cachet I Sellman
(74) *Attorney, Agent, or Firm* — Kevin M. Johnson

(57) ABSTRACT

Described herein are various antimicrobial glass articles that have improved resistance to discoloration when exposed to harsh conditions. The improved antimicrobial glass articles described herein generally include a glass substrate that has a low concentration of nonbridging oxygen atoms, a compressive stress layer and an antimicrobial silver-containing region that each extend inward from a surface of the glass substrate to a specific depth, such that the glass article experiences little-to-no discoloration when exposed to harsh conditions. Methods of making and using the glass articles are also described.

25 Claims, 7 Drawing Sheets

(56) References Cited

U.S. PATENT DOCUMENTS

| | | | | |
|---|---|---|---|---|
| 3,210,285 | A * | 10/1965 | Gangwisch | C11D 3/14 510/238 |
| 4,086,178 | A * | 4/1978 | Walker | C11D 1/004 510/180 |
| 4,191,547 | A * | 3/1980 | Wu | C03C 3/085 365/119 |
| 5,147,686 | A | 9/1992 | Ichimura et al. | 427/217 |
| 6,831,028 | B1 | 12/2004 | Ishii et al. | 501/33 |
| 6,921,546 | B2 | 7/2005 | Albach | 424/618 |
| 7,192,602 | B2 | 3/2007 | Fechner et al. | 424/405 |
| 8,034,732 | B2 | 10/2011 | Kobayashi et al. | 501/71 |
| 8,969,226 | B2 | 3/2015 | Dejneka et al. | |
| 9,156,724 | B2 | 10/2015 | Gross | |
| 9,346,703 | B2 | 5/2016 | Bookbinder et al. | |
| 2004/0166173 | A1 | 8/2004 | Albach | 424/618 |
| 2005/0069592 | A1 | 3/2005 | Fechner et al. | 424/604 |
| 2006/0142413 | A1 | 6/2006 | Zimmer et al. | |
| 2006/0172877 | A1 | 8/2006 | Fechner et al. | |
| 2007/0072392 | A1 * | 3/2007 | Ooseki | H01L 27/14683 438/455 |
| 2007/0122356 | A1 | 5/2007 | Kessler et al. | 424/49 |
| 2007/0172661 | A1 | 7/2007 | Fechner et al. | 428/409 |
| 2007/0256703 | A1 * | 11/2007 | Ikuta | B08B 7/0035 134/1 |
| 2008/0063728 | A1 | 3/2008 | Fechner et al. | 424/618 |
| 2008/0153068 | A1 | 6/2008 | Kessler et al. | 433/217.1 |
| 2009/0060967 | A1 | 3/2009 | Kamiya et al. | 424/409 |
| 2009/0142568 | A1 | 6/2009 | Dejneka et al. | |
| 2009/0162695 | A1 | 6/2009 | Hevesi et al. | 428/698 |
| 2009/0324990 | A1 * | 12/2009 | Pilloy | C03C 17/34 428/615 |
| 2010/0004111 | A1 | 1/2010 | Kobayashi et al. | 501/32 |
| 2010/0099203 | A1 * | 4/2010 | Chang | G01N 33/54393 436/519 |
| 2010/0190004 | A1 * | 7/2010 | Gibbins | A61F 13/02 428/346 |
| 2011/0081542 | A1 * | 4/2011 | Pilloy | C03C 17/34 428/341 |
| 2011/0222827 | A1 | 9/2011 | Sugawara | 385/120 |
| 2011/0250450 | A1 | 10/2011 | Naik et al. | 428/374 |
| 2012/0034435 | A1 * | 2/2012 | Borrelli | C03C 17/30 428/210 |
| 2012/0048604 | A1 * | 3/2012 | Cornejo | C03C 15/00 174/258 |
| 2012/0083750 | A1 | 4/2012 | Sansoucy | 604/265 |
| 2012/0219792 | A1 | 8/2012 | Yamamoto et al. | 428/336 |
| 2013/0276885 | A1 * | 10/2013 | Chen | H01L 31/0322 136/262 |
| 2014/0370302 | A1 * | 12/2014 | Amin | C03C 21/005 428/426 |
| 2017/0029325 | A1 * | 2/2017 | Martin | C03C 21/002 |

FOREIGN PATENT DOCUMENTS

| | | | | |
|---|---|---|---|---|
| AU | 2002349533 | A1 | 10/2003 | A01N 59/16 |
| AU | 2005315564 | A1 | 6/2006 | C03C 17/00 |
| AU | 2007263059 | A1 | 12/2007 | C23C 14/06 |
| AU | 2005315564 | B2 | 4/2011 | C03C 17/00 |
| AU | 2012263664 | A1 | 1/2013 | C23C 14/06 |
| CA | 1335705 | C | 5/1995 | C01G 23/00 |
| CA | 2268478 | A1 | 2/1999 | A61K 6/083 |
| CA | 2458425 | A1 | 8/2004 | C03C 17/06 |
| CA | 2591036 | A1 | 6/2006 | C03C 17/00 |
| CN | 1557756 | A | 12/2004 | C03C 17/06 |
| CN | 1202034 | C | 5/2005 | A01N 59/16 |
| CN | 1281539 | C | 10/2006 | C03C 12/00 |
| CN | 1856453 | A | 11/2006 | C03C 12/00 |
| CN | 1937989 | A | 3/2007 | A61K 6/083 |
| CN | 100338143 | C | 9/2007 | C08L 101/00 |
| CN | 101151405 | A | 3/2008 | D01F 1/10 |
| CN | 100413799 | C | 8/2008 | C03C 4/00 |
| CN | 100421674 | C | 10/2008 | A61K 33/30 |
| CN | 101298364 | A | 11/2008 | C03C 3/089 |
| CN | 101358669 | A | 2/2009 | F16L 9/14 |
| CN | 201206674 | Y | 3/2009 | F16L 9/14 |
| CN | 101473058 | A | 7/2009 | C23C 14/06 |
| CN | 101151405 | B | 12/2010 | D01F 1/10 |
| CN | 101298364 | B | 2/2011 | C03C 3/089 |
| CN | 101389577 | B | 5/2011 | C03C 4/02 |
| DE | 69812878 | T2 | 1/2004 | A61L 2/16 |
| EP | 333118 | B1 | 9/1992 | C01G 23/00 |
| EP | 942351 | A1 | 9/1999 | A61L 2/16 |
| EP | 942351 | B1 | 4/2003 | A61L 2/16 |
| EP | 1449816 | A1 | 8/2004 | C03C 17/06 |
| EP | 1463688 | A2 | 10/2004 | A61K 8/00 |
| EP | 1463688 | B1 | 7/2005 | A61K 8/00 |
| EP | 1470088 | B1 | 12/2005 | A61L 29/00 |
| EP | 1419119 | B1 | 5/2006 | A61F 13/49 |
| EP | 1667940 | A1 | 6/2006 | C03C 21/00 |
| EP | 1667941 | A1 | 6/2006 | C03C 21/00 |
| EP | 1744993 | A1 | 1/2007 | C03B 19/08 |
| EP | 1667941 | B1 | 5/2007 | C03C 21/00 |
| EP | 1828071 | A1 | 9/2007 | C03C 17/00 |
| EP | 2038449 | A1 | 12/2007 | C23C 14/06 |
| EP | 1580172 | B1 | 1/2010 | C03C 3/16 |
| EP | 1828071 | B1 | 2/2011 | C03C 17/00 |
| EP | 2354821 | A1 | 8/2011 | G02B 6/06 |
| JP | 3146436 | A | 6/1991 | A01N 25/00 |
| JP | 5271029 | A | 10/1993 | A01N 59/16 |
| JP | 6100329 | A | 4/1994 | A01N 25/08 |
| JP | 6254323 | A | 9/1994 | B01D 39/20 |
| JP | 7206566 | A | 8/1995 | A01N 59/16 |
| JP | 7229057 | A | 8/1995 | C03C 25/10 |
| JP | 7291654 | A | 11/1995 | C03C 3/064 |
| JP | 8165208 | A | 6/1996 | A61L 2/18 |
| JP | 8231811 | A | 9/1996 | A61L 2/16 |
| JP | 9067143 | A | 3/1997 | A01N 59/16 |
| JP | 9230552 | A | 9/1997 | B42D 15/10 |
| JP | 9326176 | A | 12/1997 | B65D 85/57 |
| JP | 10101514 | A | 4/1998 | C03C 13/00 |
| JP | 10152579 | A | 6/1998 | C08L 5/00 |
| JP | 10158037 | A | 6/1998 | A01N 59/16 |
| JP | 10158432 | A | 6/1998 | C08L 5/00 |
| JP | 11029343 | A | 2/1999 | C03C 3/064 |
| JP | 11049625 | A | 2/1999 | A61K 6/00 |
| JP | 11060268 | A | 3/1999 | C03C 4/00 |
| JP | 11060270 | A | 3/1999 | C03C 10/04 |
| JP | 11060277 | A | 3/1999 | E04F 13/15 |
| JP | 11110133 | A | 4/1999 | A61L 2/16 |
| JP | 11174628 | A | 7/1999 | B42F 5/00 |
| JP | 11209143 | A | 8/1999 | C03C 3/091 |
| JP | 11228173 | A | 8/1999 | C03C 3/062 |
| JP | 11228186 | A | 8/1999 | C03C 21/00 |
| JP | 11263629 | A | 9/1999 | A61L 2/16 |
| JP | 2000072483 | A | 3/2000 | E04F 13/15 |
| JP | 2000072487 | A | 3/2000 | C03C 17/32 |
| JP | 2000169185 | A | 6/2000 | C03C 4/00 |
| JP | 2000203876 | A | 7/2000 | C03C 3/064 |
| JP | 2000264674 | A | 9/2000 | C03C 4/00 |
| JP | 2000282389 | A | 10/2000 | D06M 13/35 |
| JP | 2000302478 | A | 10/2000 | C03C 4/00 |
| JP | 2000313624 | A | 11/2000 | C03B 8/02 |
| JP | 2000327364 | A | 11/2000 | C03C 4/00 |
| JP | 2001026466 | A | 1/2001 | C02F 1/50 |
| JP | 2001097735 | A | 4/2001 | C02F 1/50 |
| JP | 2001122638 | A | 5/2001 | C03C 4/00 |
| JP | 03199354 | B2 | 8/2001 | A61L 24/00 |
| JP | 2001226139 | A | 8/2001 | C03C 4/00 |
| JP | 2001240426 | A | 9/2001 | A01N 25/34 |
| JP | 03218096 | B2 | 10/2001 | A01N 25/08 |
| JP | 03218266 | B2 | 10/2001 | C03C 25/10 |
| JP | 03248279 | B2 | 1/2002 | C03C 3/064 |
| JP | 2002037643 | A | 2/2002 | C03C 4/00 |
| JP | 2003003075 | A | 1/2003 | C08J 3/20 |
| JP | 2003054990 | A | 2/2003 | C03C 8/14 |
| JP | 2003166155 | A | 6/2003 | A01N 25/34 |
| JP | 2003206139 | A | 7/2003 | C03B 8/02 |
| JP | 2003292341 | A | 10/2003 | C03C 12/00 |
| JP | 2003292345 | A | 10/2003 | C03C 17/22 |
| JP | 03486951 | B2 | 1/2004 | C03C 3/074 |
| JP | 2004030739 | A | 1/2004 | G11B 7/24 |
| JP | 2004067753 | A | 3/2004 | C08L 51/04 |

(56) References Cited

FOREIGN PATENT DOCUMENTS

| | | | | |
|---|---|---|---|---|
| JP | 2004073536 A | 3/2004 | ............ | A47F 3/04 |
| JP | 2004196960 A | 7/2004 | ............ | A01N 25/08 |
| JP | 2004250327 A | 9/2004 | ............ | C03C 17/06 |
| JP | 2004359753 A | 12/2004 | ............ | C08L 25/12 |
| JP | 2004359754 A | 12/2004 | ............ | C03C 12/00 |
| JP | 2004359755 A | 12/2004 | ............ | C03C 3/19 |
| JP | 03622752 B2 | 2/2005 | ............ | A01N 59/16 |
| JP | 2005047802 A | 2/2005 | ............ | C03C 12/00 |
| JP | 2005146058 A | 6/2005 | ............ | C03C 12/00 |
| JP | 2005255517 A | 9/2005 | ............ | C03C 4/00 |
| JP | 2006076854 A | 3/2006 | ............ | C03C 4/00 |
| JP | 03797951 B2 | 7/2006 | ............ | C03C 12/00 |
| JP | 03797952 B2 | 7/2006 | ............ | C03C 12/00 |
| JP | 03845852 B2 | 11/2006 | ............ | C03C 3/062 |
| JP | 03845959 B2 | 11/2006 | ............ | C03C 3/064 |
| JP | 03845975 B2 | 11/2006 | ............ | C03C 4/00 |
| JP | 2007021302 A | 2/2007 | ............ | C02F 1/50 |
| JP | 03949657 B2 | 7/2007 | ............ | A01N 25/08 |
| JP | 04052836 B2 | 2/2008 | ............ | C03B 8/02 |
| JP | 03140099 U | 3/2008 | ............ | C02F 1/50 |
| JP | 2008087778 A | 4/2008 | ............ | B65D 81/28 |
| JP | 04086893 B2 | 5/2008 | ............ | D01F 1/10 |
| JP | 04095604 B2 | 6/2008 | ............ | C03C 3/19 |
| JP | 2008133583 A | 6/2008 | ............ | D01F 1/10 |
| JP | 2008214131 A | 9/2008 | ............ | C03C 12/00 |
| JP | 04163778 B2 | 10/2008 | ............ | C03C 3/091 |
| JP | 2008308437 A | 12/2008 | ............ | A01N 25/04 |
| JP | 04212642 B2 | 1/2009 | ............ | C03C 4/02 |
| JP | 2009023877 A | 2/2009 | ............ | C03C 12/00 |
| JP | 04387163 B2 | 12/2009 | ............ | C03C 12/00 |
| JP | 2010088980 A | 4/2010 | ............ | C02F 1/50 |
| JP | 2010122436 A | 6/2010 | ............ | G02B 6/06 |
| JP | 2010144362 A | 7/2010 | ............ | E04B 1/76 |
| JP | 04557546 B2 | 10/2010 | ............ | A61K 8/00 |
| JP | 04700720 B2 | 6/2011 | ............ | C02F 1/50 |
| JP | 04723558 B2 | 7/2011 | ............ | D01F 1/10 |
| JP | 04804669 B2 | 11/2011 | ............ | C03C 8/14 |
| JP | 2011241107 A | 12/2011 | ............ | C03C 21/00 |
| JP | 2012007870 A | 1/2012 | ............ | F24F 13/22 |
| JP | 2012010915 A | 1/2012 | ............ | A47G 27/02 |
| JP | 2012161728 A | 8/2012 | ............ | C02F 1/50 |
| JP | 05027349 B1 | 9/2012 | ............ | C08L 67/02 |
| JP | 05043393 B2 | 10/2012 | ............ | B65D 81/28 |
| JP | 05069482 B2 | 11/2012 | ............ | C03C 12/00 |
| JP | 05085803 B2 | 11/2012 | ............ | C03C 12/00 |
| JP | 2012214381 A | 11/2012 | ............ | C03C 12/00 |
| JP | 05131786 B2 | 1/2013 | ............ | F24F 13/22 |
| JP | 2013000441 A | 1/2013 | ............ | A45D 34/04 |
| KR | 2004075283 A | 8/2004 | ............ | C03C 17/06 |
| KR | 2007087050 A | 8/2007 | ............ | C03C 17/06 |
| KR | 2007112482 A | 11/2007 | ............ | D01F 1/10 |
| KR | 961604 B1 | 6/2010 | ............ | D01F 1/10 |
| KR | 2010092841 A | 8/2010 | ............ | C03C 4/00 |
| KR | 2010092842 A | 8/2010 | ............ | C03C 3/00 |
| KR | 2011086546 A | 7/2011 | ............ | G02B 6/06 |
| KR | 1174402 B1 | 8/2012 | ............ | C03C 17/22 |
| KR | 2012117495 A | 10/2012 | ............ | C03C 21/00 |
| MX | 2004PA001649 A | 8/2004 | ............ | C03C 17/06 |
| PT | 1828071 E | 5/2011 | ............ | C03C 17/00 |
| RU | 2404142 C2 | 11/2010 | ............ | C03C 17/36 |
| SG | 158898 A1 | 2/2010 | | |
| SG | 172722 A1 | 7/2011 | | |
| TW | 498261 B | 8/2002 | ............ | A61L 2/16 |
| WO | 1999007326 A2 | 2/1999 | ............ | A61K 6/083 |
| WO | 1999017188 A1 | 4/1999 | ............ | A61L 2/16 |
| WO | 1999007326 A3 | 5/1999 | ............ | A61K 6/083 |
| WO | WO2003050053 A3 | 9/2003 | ............ | A61K 8/00 |
| WO | 2003082758 A1 | 10/2003 | ............ | A01N 59/16 |
| WO | 2005042437 A2 | 5/2005 | ............ | A01N 59/16 |
| WO | 2005087675 A1 | 9/2005 | ............ | A01N 25/08 |
| WO | 2006120772 A1 | 11/2006 | ............ | D01F 1/10 |
| WO | 2007108245 A1 | 9/2007 | ............ | C03C 4/02 |
| WO | 2005042437 A3 | 8/2009 | ............ | C03C 21/00 |
| WO | 2011058345 A2 | 5/2011 | ............ | A61K 6/02 |
| WO | WO2011088298 A1 | 7/2011 | ............ | A01N 25/34 |
| WO | 2011145592 A1 | 11/2011 | ............ | C03C 21/00 |
| WO | 2011148528 A1 | 12/2011 | ............ | C03C 4/00 |
| WO | 2012098742 A1 | 7/2012 | ............ | C08L 67/02 |
| WO | 2012107435 A1 | 8/2012 | ............ | C08K 3/00 |
| WO | 2012135294 A2 | 10/2012 | ............ | A01N 59/20 |
| WO | 2012176760 A1 | 12/2012 | ............ | B29C 49/00 |
| WO | 2013055994 A1 | 4/2013 | ............ | A01N 25/08 |

OTHER PUBLICATIONS http://microbewiki.kenyon.edu/index.php/Silver_as_an_Antimicrobial_Agent.

Peter HM Hoet,1 Irene Brüske-Hohlfeld,2 and Oleg V Salata, Nanoparticles—known and unknown health risks, J Nanobiotechnology. 2004; 2: 12.

F. Verrier, K. Matias, D. Fiacco, Y. Wei, and J. Lynn, "New Antibacterial Test Method for Evaluating the Efficacy of Silver Glass as Sanitizer", Redlines Journal, vol. 5, No. 2, Paper 11, Nov. 2012.

Yuan Xun, M.I. Setyawati, A. S. Tan, C. N. Ong, D.T. Leong and J. Xie, "Highly luminescent silver nanoclusters with tunable emissions: cyclic reduction—decomposition synthesis and antimicrobial properties", NPG Asia Materials, vol. 5, 2013 p. 1-8.

T. Ahmed, S. Imdad, D. Ashraf, N. M. Butt, "Effect of size and surface ligands of silver (Ag) nanoparticles on waterborne bacteria", Int. J. Of Theoretical and Appl. Nanotech. vol. 1 Issue 1 2012.

A. A. El-Kheshen and S.F. GadEl-Rab, "Effect of reducing and protecting agents on size of silver nanoparticles and their ant -bacteriial activity", Der Pharma Chemica, 4(1) 2012 pp. 53-65.

Heats of Solution of Solids in Molten Reciprocal Salt Systems., M. Blander , J. Braunstein , M. D. Silverman. J. Am. Chem. Soc., 1963, 85 (7), pp. 895-897.

Y. Lin and W. Tseng, "Highly sensitive detection of silver ions and silver nanoparticles in aqueous solutions iusing an oligonucleic-based fluorogenic probe", Chem Comm. 2009, 6619-6621.

http://en.wikipedia.org/wiki/RCA_clean.

J.Gregory Couillard, Dieter G. Ast, Christopher Umbach, Jack M. Blakely, Chad B. Moore, Francis P. Fehlner, "Chemical treatment of glass substrates", Journal of Non-Crystalline Solids, vol. 222, Dec. 2, 1997, pp. 429-434.

D.M. Mattox, Handbook of Physical Vapor Deposition (PVD) Processes, Elsevier Inc., 2010.

* cited by examiner

ANTIMICROBIAL GLASS ARTICLES AND METHODS OF MAKING AND USING SAME

This application claims the benefit of priority under 35 U.S.C. § 119 of U.S. Provisional Application Ser. No. 61/835,959, filed on Jun. 17, 2013, the content of which is relied upon and incorporated herein by reference in its entirety.

BACKGROUND

The present disclosure relates generally to antimicrobial glass articles. More particularly, the various embodiments described herein relate to glass articles having antimicrobial behavior, such that the glass articles exhibit reduced discoloration when exposed to harsh conditions (e.g., elevated temperatures, humidity, oxidizing environments, reducing environments, and/or the like) while maintaining antimicrobial efficacy, as well as to methods of making, using and cleaning of the glass articles.

Touch-activated or -interactive devices, such as screen surfaces (e.g., surfaces of electronic devices having user-interactive capabilities that are activated by touching specific portions of the surfaces), have become increasingly more prevalent. In general, these surfaces should exhibit high optical transmission, low haze, and high durability, among other features. As the extent to which the touch screen-based interactions between a user and a device increases, so too does the likelihood of the surface harboring microorganisms (e.g., bacteria, fungi, viruses, and the like) that can be transferred from user to user.

To minimize the presence of microbes on glass, so-called "antimicrobial" properties have been imparted to a variety of glass articles. Such antimicrobial glass articles, regardless of whether they are used as screen surfaces of touch-activated devices or in other applications, have a propensity to discolor for various reasons. For example, one reason incudes the presence of silver particles (including nano-silver particles) on the surface of the glass or the presence of reduced silver due to exposure to elevated temperatures, humidity, reactive environments, and/or the like. These harsh conditions can occur during fabrication or processing of the glass articles, or during ordinary use of the articles. In certain cases, this discoloration can render a glass article unsightly. Further, excessive discoloration ultimately can lead to the glass article becoming unsuitable for its intended purpose.

There accordingly remains a need for technologies that provide antimicrobial glass articles with improved resistance against discoloration when exposed to harsh conditions. It would be particularly advantageous if such technologies did not adversely affect other desirable properties of the surfaces (e.g., optical transmission, haze, strength, scratch resistance, and the like). It is to the provision of such technologies that the present disclosure is directed.

BRIEF SUMMARY

Described herein are various antimicrobial glass articles that have improved resistance to discoloration when exposed to harsh conditions, along with methods for their manufacture and use.

One type of improved antimicrobial glass article includes a glass substrate that has a compressive stress layer or region that extends inward from a surface of the glass substrate to a first depth, and an antimicrobial silver-containing layer or region that extends inward from the surface of the glass substrate to a second depth, such that the glass article experiences substantially no discoloration when exposed to harsh conditions.

This type of antimicrobial glass article can further include an additional layer disposed on the surface of the glass substrate. The additional layer can include a reflection-resistant coating, a glare-resistant coating, fingerprint-resistant coating, smudge-resistant coating, a color-providing composition, an environmental barrier coating, or an electrically conductive coating.

In one or more embodiments, the glass substrate may have a low concentration of nonbridging oxygens (NBOs). A mechanism for the reduction of silver, and thus the discoloration due to exposure to harsh conditions, can be related to the concentration of NBOs in the glass substrate. The measure of the concentration of NBOs is proportional to the quantity (alumina mol %–total alkali mol %). In one or more embodiments the antimicrobial glass article may include a glass substrate with a low concentration of NBOs such that the difference between (alumina mol %–total alkali mol %) in the glass substrate may be greater than or equal ($\geq$) to about −1 mol % or, more specifically, greater than or equal ($\geq$) to about 0 mol %.

In certain implementations of this type of improved antimicrobial glass article, a compressive stress of the compressive stress layer can be about 200 megapascals to about 1.2 gigapascals, and/or the depth of the compressive stress layer can be greater than or equal to about 25 micrometers ($\mu$m) and less than or equal to about 100 micrometers ($\mu$m).

In some implementations of this type of improved antimicrobial glass article, the antimicrobial silver-containing region can have an average thickness of less than or equal to about 20 micrometers ($\mu$m). A silver concentration in an outermost portion of such an antimicrobial silver-containing region can be greater than about 5 weight percent and, in some cases, up to about 45 weight percent, based on the total weight of the antimicrobial silver-containing region.

In other implementations of this type of improved antimicrobial glass article, the antimicrobial silver-containing region can have an average thickness of up to about 150 micrometers ($\mu$m) and, in some instances, in a range from about 20 micrometers ($\mu$m) to about 150 micrometers ($\mu$m). A silver concentration in an outermost portion of such an antimicrobial silver-containing region can be up to about 6 weight percent.

The harsh conditions can include temperatures of greater than or equal to about 180 degrees Celsius, relative humidity levels of greater than or equal to about 50 percent, reducing environments or a combination thereof. For example, the harsh conditions can include polymerization of a fingerprint- and/or smudge-resistant coating on the surface of the glass substrate at elevated temperatures, direct bonding of an adhesive used to adhere the glass substrate to another device, sputtering of a transparent electrode on the surface of the glass substrate, thermal curing of an ink layer on the surface of the glass substrate, plasma cleaning of the surface of the glass substrate, chemical etching of the surface of the glass substrate, annealing of the surface of the glass substrate, chemical cleaning of the surface of the glass substrate, or a combination thereof. In some embodiments, exposure to harsh conditions can include exposure to harsh conditions for about 1.5 hours or more, about 2 hours or more, about 2.5 hours or more, about 3 hours or more, or even about 4 hours or more.

Substantially no discoloration can include a change in optical transmittance of the glass article of less than or equal to about 3 percent relative to an optical transmittance before exposure to the harsh conditions, a change in haze of the glass article of less than or equal to about 5 percent relative to a haze before exposure to the harsh conditions, and/or a change in CIE 1976 color coordinates L*, a*, and b* of the glass article of less than or equal to about ±0.2, ±0.1, and ±0.1, respectively. In some embodiments, the change in CIE 1976 color coordinates L*, a* and b* of the antimicrobial glass article is less than or equal to about ±0.1, ±0.05, ±0.05, respectively.

This type of antimicrobial glass article can exhibit at least a 5 log reduction in a concentration of at least *Staphylococcus aureus, Enterobacter aerogenes,* and *Pseudomonas aeruginosa* bacteria under JIS Z 2801 (2000) testing conditions. This type of antimicrobial glass article can also exhibit at least a 3 log reduction in a concentration of at least *Staphylococcus aureus, Enterobacter aerogenes,* and *Pseudomonas aeruginosa* bacteria under modified JIS Z 2801 (2000) testing conditions, wherein the modified conditions comprise heating the antimicrobial glass article to a temperature of about 23 degrees Celsius to about 37 degrees Celsius at a humidity of about 38 percent to about 42 percent for about 6 hours. This type of antimicrobial glass article can also exhibit ≤2 log reduction in a concentration of at least *Staphylococcus aureus, Enterobacter aerogenes,* and *Pseudomonas aeruginosa* bacteria under modified EPA testing conditions, wherein the modified conditions comprise heating the antimicrobial glass article to a temperature of about 23 degrees Celsius at a humidity of about 38 percent to about 42 percent for about 2 hours.

This type of improved antimicrobial glass article can serve as a portion of a touch-sensitive display screen or cover plate for an electronic device, a non-touch-sensitive component of an electronic device, a surface of a household appliance, a surface of medical equipment, a biological or medical packaging vessel, or a surface of a vehicle component.

One type of method of making an antimicrobial glass article includes providing a glass substrate having a low concentration of nonbridging oxygens, forming a compressive stress layer that extends inward from a surface of the glass substrate to a first depth, and forming an antimicrobial silver-containing region that extends inward from the surface of the glass substrate to a second depth, such that the glass article undergoes substantially no discoloration when exposed to harsh conditions.

In some cases, the method can also include forming an additional layer on at least a portion of the surface of the substrate, wherein the additional layer comprises a reflection-resistant coating, a glare-resistant coating, fingerprint-resistant coating, smudge-resistant coating, a color-providing composition, an environmental barrier coating, or an electrically conductive coating.

In some implementations, the step of forming the compressive stress layer can include contacting the glass substrate with a $KNO_3$-containing molten salt bath for about 30 minutes to about 24 hours, during which the $KNO_3$-containing molten salt bath has a temperature of about 380 degrees Celsius to about 460 degrees Celsius, and the step of forming the antimicrobial silver-containing region can include contacting the glass substrate comprising the compressive stress layer with a $AgNO_3$-containing molten salt bath for about 5 minutes to about 18 hours, during which the $AgNO_3$-containing molten salt bath has a temperature of about 300 degrees Celsius to about 400 degrees Celsius. The $KNO_3$-containing molten salt bath can include $KNO_3$ and a poisoning component selected from $NaNO_3$ or $LiNO_3$, wherein the poisoning component comprises up to about 10 weight percent of the $KNO_3$-containing molten salt bath, based on a total weight of the $KNO_3$-containing molten salt bath. The $AgNO_3$-containing molten salt bath can include $AgNO_3$ and $KNO_3$, wherein the $KNO_3$ comprises about 75 weight percent to about 99.95 weight percent of the $AgNO_3$-containing molten salt bath, based on a total weight of the $AgNO_3$-containing molten salt bath. The $AgNO_3$-containing molten salt bath can further include a poisoning component in an amount that is less than an amount of the $AgNO_3$ in the $AgNO_3$-containing molten salt bath and/or less than or equal to an amount of the poisoning component in the $KNO_3$-containing molten salt bath.

In some cases, the antimicrobial silver-containing region has an average thickness of less than or equal to about 10 micrometers. In these cases, a silver concentration at an outermost 50 nanometers of the antimicrobial silver-containing region can be up to about 45 weight percent, based on a total weight of this outermost 50 nanometers of the antimicrobial silver-containing region.

In some cases, the step of forming the compressive stress layer and the step of forming the antimicrobial silver-containing region occur simultaneously.

In some implementations, the method can also include a chemical cleaning treatment after the antimicrobial silver-containing region is formed. Chemically cleaning the glass substrate can entail contacting the glass substrate with a cleaning solution at an ambient temperature for less than or equal to about 15 minutes, wherein the cleaning solution includes less than or equal to about 2 volume percent each of ammonium hydroxide and hydrogen peroxide in water, based on a total volume of the cleaning solution.

In additional implementations, chemically cleaning the glass substrate can entail contacting the glass substrate with a dilute, aqueous cleaning solution comprising a chloride (e.g., sodium chloride) for less than or equal to about 15 minutes. When sodium chloride is the chloride employed in this aqueous cleaning solution, it can range from about 0.01 wt % to about 5 wt %. The aqueous chloride cleaning solution can be held at temperatures above ambient during the contacting of the glass substrate. For example, the aqueous chloride cleaning solution can be held at from 30° C. to about 90° C. during the step of contacting the glass substrate.

In further implementations, chemical cleaning of the glass substrate can include contacting the glass substrate with a dilute, aqueous cleaning solution comprising citric acid for less than or equal to about 15 minutes. In some implementations, the citric acid can range from about 0.01 wt % to about 5 wt %. The aqueous, citric acid-containing cleaning solution can be held at temperatures above ambient during the contacting of the glass substrate. For example, the aqueous cleaning solution containing citric acid can be held at from 30° C. to about 90° C. during the step of contacting the glass substrate. In an embodiment, the temperature of the aqueous citric acid-containing solution is held at about 50° C. to about 70° C. during the contacting of the glass substrate.

Contacting the glass substrate with a cleaning solution (e.g., aqueous solutions containing ammonium hydroxide/ hydrogen peroxide, chlorides or citric acid) can involve ultrasonic agitation, e.g., during the application of the cleaning solution. In some cases, the chemical cleaning treatment can further include rinsing and/or drying the glass substrate. The rinsing can involve contacting the glass substrate with a rinsing agent after contacting the glass substrate with the cleaning solution. In one such case, contacting the glass substrate with a rinsing agent can entail immersing the glass substrate in the rinsing agent, which can include the use of ultrasonic agitation, followed by spraying the glass substrate with the rinsing agent. During these steps, the rinsing agent can be deionized water and can have a temperature of less than or equal to about 60 degrees Celsius.

It is to be understood that both the foregoing brief summary and the following figures and detailed description describe various embodiments and are intended to provide an overview or framework for understanding the nature and character of the claimed subject matter.

DETAILED DESCRIPTION

Figure 1:
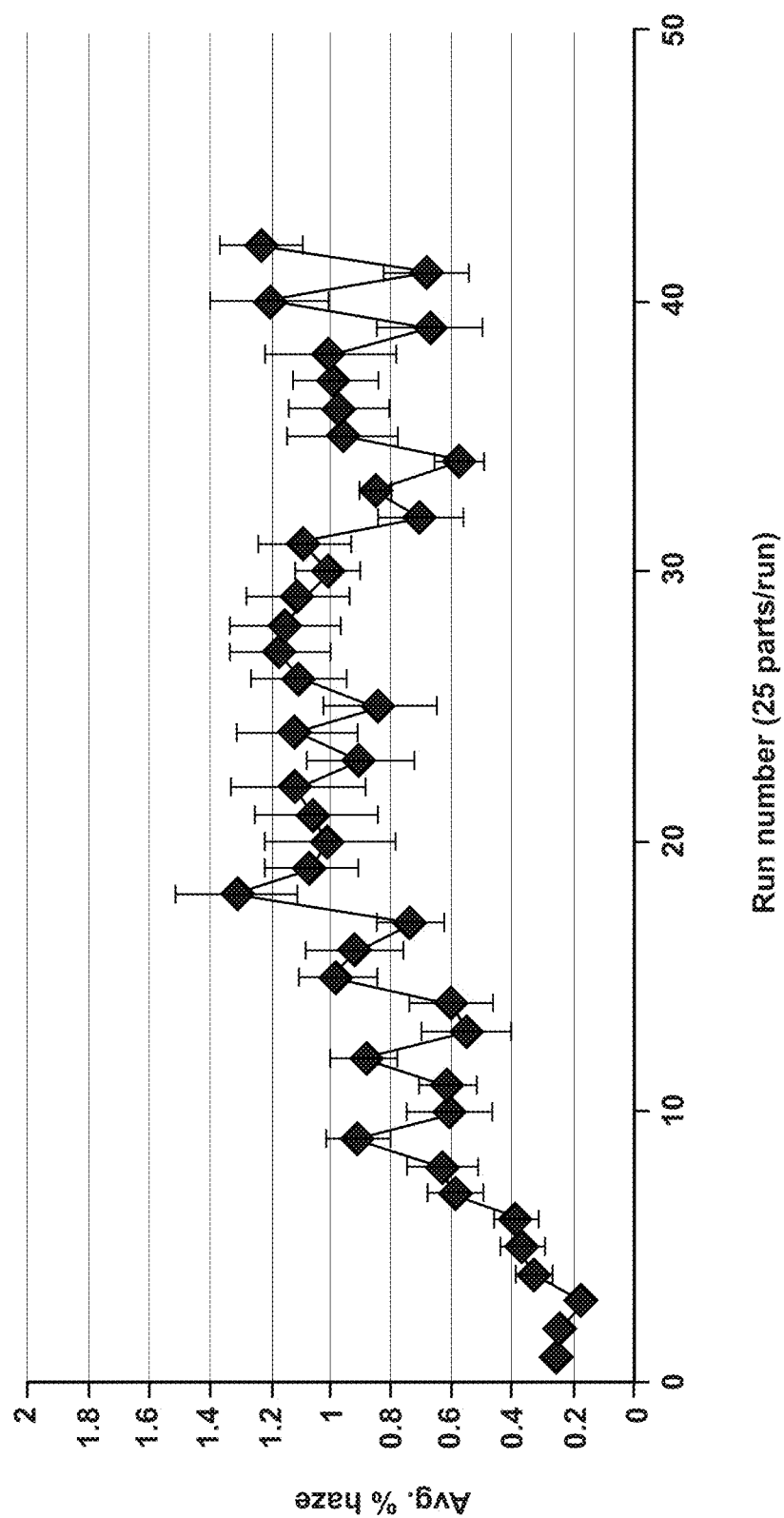
FIG. 1 1 includes a graph of average haze of known antimicrobial glass articles fabricated over a period of time in multiple runs.

Throughout this description, various components may be identified having specific values or parameters. These items, however, are provided as being exemplary of the present disclosure. Indeed, the exemplary embodiments do not limit the various aspects and concepts, as many comparable parameters, sizes, ranges, and/or values may be implemented. Similarly, the terms "first," "second," "primary," "secondary," "top," "bottom," "distal," "proximal," and the like, do not denote any order, quantity, or importance, but rather are used to distinguish one element from another. Further, the terms "a," "an," and "the" do not denote a limitation of quantity, but rather denote the presence of "at least one" of the referenced item.

Described herein are various antimicrobial glass articles that have improved haze, while exhibiting the same antimicrobial efficacy and strength. The term "antimicrobial" refers herein to the ability to kill or inhibit the growth of more than one species of more than one type of microbe (e.g., bacteria, viruses, fungi, and the like). In one or more embodiments, the article exhibits a haze that is tailored to the particular application. As used herein, the terms "haze" and "transmission haze" refer to the percentage of transmitted light scattered outside an angular cone of ±4.0° in accordance with ASTM procedure D1003, the contents of which are incorporated herein by reference in their entirety as if fully set forth below. For an optically smooth surface, transmission haze is generally close to zero. In those situations when the antimicrobial glass article is used in the construction of a touch screen for an electronic device, the haze of the article can be less than or equal to about 1%.

Embodiments of the antimicrobial articles described herein exhibit resistance to discoloration when exposed to harsh conditions (i.e., during manufacture and/or use of the articles), along with methods for their manufacture and use. In general, the improved articles and methods described herein involve the use of a glass substrate that has a low concentration of nonbridging oxygens (NBOs). As used herein, the term "nonbridging oxygens" is intended to refer to those oxygen atoms within the glass that bear a negative charge that can be compensated by a vicinal positively charged ion. For example, where silicon is bonded to four oxygen atoms and where the bond between the silicon atom and one of the oxygen atoms is broken, that oxygen atom bears a negative charge, which may be compensated by an alkali atom (e.g., Na). This is in contrast to those oxygen atoms within the glass that are covalently bonded to other atoms and do not bear a negative charge (such oxygen atoms being termed "bridging oxygens"). One way to determine the concentration of NBOs includes subtracting the sum of the concentrations, in mole percent (mol %), of all alkali metal oxides from the concentration, in mol %, of aluminum oxide. That is, NBO concentration is proportional to ($Al_2O_3$ (mol %)−(Σ alkali metal oxides (mol %)). It is important to note that, because of this particular NBO concentration calculation, NBO concentration values can be negative. Thus, in some implementations of the glass articles, the concentration of NBOs will be less than zero. Where the difference $Al_2O_3$ (mol %)−(Σ alkali metal oxides (mol %)) equals zero or a positive number, then there are no NBOs present. Where the difference $Al_2O_3$ (mol %)−(Σ alkali metal oxides (mol %)) equals a negative number, that negative number indicates the presence of NBOs.

Discoloration in antimicrobial glass articles can occur when there is a residue on a surface thereof. In some instances, the residue imparts haze or causes haze in the articles. The residue of one or more embodiments can include particulates including nano-particles, which can include silver. In one or more embodiments, discoloration can also occur in the antimicrobial glass articles when NBOs present in a glass substrate provide an electron to an $Ag^+$ ion, thus reducing the $Ag^+$ ion to $Ag^0$. $Ag^0$ provides poor antimicrobial activity as compared to $Ag^+$. Reduced $Ag^0$ also shows a distinct plasmon resonance peak at 430 nm which appears as a color change to the eye of an observer. This cause of Ag reduction, and thus NBO-induced discoloration, due to the presence of NBOs should be distinguished from other causes of discoloration. Electrons may be present or formed in the glass substrate from other sources, such as exposure to ultraviolet light, which are unrelated to the amount of NBOs present in the glass substrate. These electrons may cause $Ag^+$ ions or other metal ions present in the glass to reduce and thus, cause discoloration of the glass substrate. This type of UV-induced discoloration can be distinguished from the discoloration attributable to the presence of NBOs.

The improved antimicrobial glass articles described herein generally include a glass substrate that has a compressive stress layer or region that extends inward from a surface of the glass substrate to a first depth, an antimicrobial silver-containing layer or region that extends inward from a surface of the glass substrate to a second depth, and a haze of about 0.9% or less, about 0.8% or less, about 0.7% or less, about 0.6% or less or about 0.5% or less. In some embodiments, the article may have a haze in the range from about 0.1% to about 0.9%, from about 0.1% to about 0.8%, from about 0.1% to about 0.7% and all ranges and subranges therebetween. Throughout this specification, the term "compressive stress layer" shall be used to refer to the layer or region of compressive stress, and the term "antimicrobial silver-containing region" shall be used to refer to the layer or region containing the antimicrobial silver species. This usage is for convenience only, and is not intended to provide a distinction between the terms "region" or "layer" in any way. In some embodiments, the antimicrobial glass article experiences little-to-no discoloration when exposed to harsh conditions.

The choice of glass used for the glass substrate is not limited to a particular composition, as improved resistance to discoloration can be obtained using a variety of glass compositions that have a low concentration of NBOs, as defined above. For example, the composition chosen can be any of a wide range of silicate, borosilicate, aluminosilicate, or boroaluminosilicate glass compositions, which optionally can comprise one or more alkali and/or alkaline earth modifiers.

By way of illustration, one family of compositions includes those having at least one of aluminum oxide or boron oxide and at least one of an alkali metal oxide or an alkali earth metal oxide, wherein −15 mol % ($R_2O+R'O-Al_2O_3-ZrO_2$)−$B_2O_3 \leq 4$ mol %, where R can be Li, Na, K, Rb, and/or Cs, and R' can be Mg, Ca, Sr, and/or Ba. One subset of this family of compositions includes from about 62 mol % to about 70 mol % $SiO_2$; from 0 mol % to about 18 mol % $Al_2O_3$; from 0 mol % to about 10 mol % $B_2O_3$; from 0 mol % to about 15 mol % $Li_2O$; from 0 mol % to about 20 mol % $Na_2O$; from 0 mol % to about 18 mol % $K_2O$; from 0 mol % to about 17 mol % MgO; from 0 mol % to about 18 mol % CaO; and from 0 mol % to about 5 mol % $ZrO_2$. Such glasses are described more fully in U.S. patent application Ser. No. 12/277,573 by Matthew J. Dejneka et al., entitled "Glasses Having Improved Toughness And Scratch Resistance," filed Nov. 25, 2008, and claiming priority to U.S. Provisional Patent Application No. 61/004,677, filed on Nov. 29, 2008, the contents of which are incorporated herein by reference in their entireties as if fully set forth below.

Another illustrative family of compositions includes those having at least 50 mol % $SiO_2$ and at least one modifier selected from the group consisting of alkali metal oxides and alkaline earth metal oxides, wherein [($Al_2O_3$ (mol %)+$B_2O_3$ (mol %))/(Σ alkali metal modifiers (mol %))]>1. One subset of this family includes from 50 mol % to about 72 mol % $SiO_2$; from about 9 mol % to about 17 mol % $Al_2O_3$; from about 2 mol % to about 12 mol % $B_2O_3$; from about 8 mol % to about 16 mol % $Na_2O$; and from 0 mol % to about 4 mol % $K_2O$. Such glasses are described in more fully in U.S. patent application Ser. No. 12/858,490 by Kristen L. Barefoot et al., entitled "Crack And Scratch Resistant Glass and Enclosures Made Therefrom," filed Aug. 18, 2010, and claiming priority to U.S. Provisional Patent Application No. 61/235,767, filed on Aug. 21, 2009, the contents of which are incorporated herein by reference in their entireties as if fully set forth below.

Yet another illustrative family of compositions includes those having $SiO_2$, $Al_2O_3$, $P_2O_5$, and at least one alkali metal oxide ($R_2O$), wherein $0.75 \leq [(P_2O_5(\text{mol \%})+R_2O(\text{mol \%}))/M_2O_3 (\text{mol \%})] \leq 1.2$, where $M_2O_3=Al_2O_3+B_2O_3$. One subset of this family of compositions includes from about 40 mol % to about 70 mol % $SiO_2$; from 0 mol % to about 28 mol % $B_2O_3$; from 0 mol % to about 28 mol % $Al_2O_3$; from about 1 mol % to about 14 mol % $P_2O_5$; and from about 12 mol % to about 16 mol % $R_2O$. Another subset of this family of compositions includes from about 40 to about 64 mol % $SiO_2$; from 0 mol % to about 8 mol % $B_2O_3$; from about 16 mol % to about 28 mol % $Al_2O_3$; from about 2 mol % to about 12 mol % $P_2O_5$; and from about 12 mol % to about 16 mol % $R_2O$. Such glasses are described more fully in U.S. patent application Ser. No. 13/305,271 by Dana C. Bookbinder et al., entitled "Ion Exchangeable Glass with Deep Compressive Layer and High Damage Threshold," filed Nov. 28, 2011, and claiming priority to U.S. Provisional Patent Application No. 61/417,941, filed Nov. 30, 2010, the contents of which are incorporated herein by reference in their entireties as if fully set forth below.

Yet another illustrative family of compositions includes those having at least about 4 mol % $P_2O_5$, wherein ($M_2O_3$ (mol %)/$R_xO$(mol %))<1, wherein $M_2O_3=Al_2O_3+B_2O_3$, and wherein $R_xO$ is the sum of monovalent and divalent cation oxides present in the glass. The monovalent and divalent cation oxides can be selected from the group consisting of $Li_2O$, $Na_2O$, $K_2O$, $Rb_2O$, $Cs_2O$, MgO, CaO, SrO, BaO, and ZnO. One subset of this family of compositions includes glasses having 0 mol % $B_2O_3$. Such glasses are more fully described in U.S. Provisional Patent Application No. 61/560,434 by Timothy M. Gross, entitled "Ion Exchangeable Glass with High Crack Initiation Threshold," filed Nov. 16, 2011, the contents of which are incorporated herein by reference in their entirety as if fully set forth below.

Still another illustrative family of compositions includes those having $Al_2O_3$, $B_2O_3$, alkali metal oxides, and contains boron cations having three-fold coordination. When ion exchanged, these glasses can have a Vickers crack initiation threshold of at least about 30 kilograms force (kgf). One subset of this family of compositions includes at least about 50 mol % $SiO_2$; at least about 10 mol % $R_2O$, wherein $R_2O$ comprises $Na_2O$; $Al_2O_3$, wherein −0.5 mol %≤$Al_2O_3$(mol %)−$R_2O$(mol %)≤2 mol %; and $B_2O_3$, and wherein $B_2O_3$ (mol %)−($R_2O$(mol %)−$Al_2O_3$(mol %))≥4.5 mol %. Another subset of this family of compositions includes at least about 50 mol % $SiO_2$, from about 9 mol % to about 22 mol % $Al_2O_3$; from about 4.5 mol % to about 10 mol % $B_2O_3$; from about 10 mol % to about 20 mol % $Na_2O$; from 0 mol % to about 5 mol % $K_2O$; at least about 0.1 mol % MgO and/or ZnO, wherein 0≤MgO+ZnO≤6 mol %; and, optionally, at least one of CaO, BaO, and SrO, wherein 0 mol %≤CaO+SrO+BaO≤2 mol %. Such glasses are more fully described in U.S. Provisional Patent Application No. 61/653,485 by Matthew J. Dejneka et al., entitled "Ion Exchangeable Glass with High Damage Resistance," filed May 31, 2012, the contents of which are incorporated herein by reference in their entirety as if fully set forth below.

In general, the concentration of NBOs, as defined above, in the glass articles can be, in mol %, ≥to about −1, ≥to about −0.9, ≥to about −0.8, ≥to about −0.7, ≥to about −0.6, ≥to about −0.5, ≥to about −0.4, ≥to about −0.3, ≥to about −0.2, ≥to about −0.1, ≥to about 0, ≥to about 0.1, ≥to about 0.2, ≥to about 0.3, ≥to about 0.4, ≥to about 0.5, ≥to about 0.6, ≥to about 0.7, ≥to about 0.8, ≥to about 0.9≥to about 1. In some embodiments, the NBO concentration may be in the range from about −1 mol % to about 20 mol %, from about −1 mol % to about 15 mol %, from about −1 mol % to about 10 mol %, from about −1 mol % to about 5 mol %, from about −1 mol % to about 4 mol %, from about −1 mol % to about 3 mol %, from about −1 mol % to about 2 mol %, from about −1 mol % to about 1 mol %, from about −1 mol % to about 0.75 mol %, from about −1 mol % to about 0.5 mol %, from about −1 mol % to about 0.25 mol %, from about −1 mol % to about 0 mol %, from about −0.75 mol % to about 1 mol %, from about −0.5 mol % to about 1 mol %, from about −0.25 mol % to about 1 mol %, from about −0.25 mol % to about 0.25 mol % and all ranges and sub-ranges therebetween.

The glass substrate can adopt a variety of physical forms. That is, from a cross-sectional perspective, the substrate can be flat or planar, or it can be curved and/or sharply-bent. Similarly, it can be a single unitary object, or a multi-layered structure or a laminate.

Regardless of its composition or physical form, the glass substrate will include a layer or region under compressive stress that extends inward from a surface of the glass substrate to a specific depth therein. This compressive stress layer can be formed from a strengthening process (e.g., by thermal tempering, chemical ion-exchange, or like processes). The amount of compressive stress (CS) and the depth of the compressive stress layer (DOL) can be varied based on the particular use for the glass article, with the proviso that the CS and DOL should be limited such that a tensile stress created within the glass as a result of the compressive stress layer does not become so excessive as to render the glass article frangible.

In addition, the glass substrate will include an antimicrobial silver-containing layer or region that extends inward from a surface of the glass substrate to a specific depth therein. The antimicrobial silver-containing region comprises cationic monovalent silver ($Ag^+$) in an amount effective to impart antimicrobial behavior to the glass article. In general, the antimicrobial silver-containing region, like the compressive stress layer, extends inward from the surface of the glass substrate. Thus the antimicrobial silver-containing region at least partially overlaps with the compressive stress layer. In some embodiments, the depth of the compressive stress layer is greater than the depth of the antimicrobial silver-containing region. In other embodiments, the depth of the compressive stress layer and the depth of the antimicrobial silver-containing region are about the same. The depth of the antimicrobial silver-containing region (DOR) may generally be limited so as to avoid visible coloration in the glass article and to maximize the antimicrobial efficacy of the cationic silver within the glass substrate.

In certain implementations, the antimicrobial glass articles can include an additional layer disposed on the surface of the glass substrate. The optional additional layer (s) can be used to provide additional features to the antimicrobial glass article (e.g., reflection resistance or anti-reflection properties, glare resistance or anti-glare properties, fingerprint resistance or anti-fingerprint properties, smudge resistance or anti-smudge properties, color, opacity, environmental barrier protection, electronic functionality, and/or the like). Materials that can be used to form the optional additional layer(s) generally are known to those skilled in the art to which this disclosure pertains.

Methods of making the above-described articles generally include the steps of providing a glass substrate as described herein, forming a compressive stress layer that extends inward from a surface of the glass substrate to a first depth, and forming an antimicrobial silver-containing region that extends inward from the surface of the glass substrate to a second depth. In those embodiments where the optional additional layer is implemented, the methods generally involve an additional step of forming the additional layer on at least a portion of the surface of the substrate.

The selection of materials used in the glass substrates and optional additional layers can be made based on the particular application desired for the final glass article. In general, however, the specific materials will be chosen from those described above.

In some embodiments, the method includes providing a glass substrate having a low concentration of NBOs, which can involve selection of a glass object as-manufactured, or it can entail subjecting the as-manufactured glass object to a treatment in preparation for any of the subsequent steps. Examples of such treatments include physical or chemical cleaning, physical or chemical etching, physical or chemical polishing, annealing, shaping, and/or the like.

Once the glass substrate has been selected and/or prepared, the compressive stress layer and/or the antimicrobial silver-containing region can be formed therein. That is, the compressive stress layer can be formed before, after, or simultaneously with the antimicrobial silver-containing region.

Formation of the compressive stress layer can be accomplished in a variety of ways, of which thermal tempering and chemical ion exchange are the most common. With thermal tempering, the glass substrate generally is heated above its annealing point, followed by a rapid cooling step to quench an outer or exterior region of the glass substrate in a compressed state, while an interior region of the glass cools at a slower rate and is placed under tension. The heating temperature, heating time, and cooling rate are generally the primary parameters that can be tailored to achieve a desired CS and DOL in the compressive stress layer (the exterior region of the glass substrate in a compressed state).

In contrast, with chemical ion exchange, the glass substrate is contacted with a molten salt bath (e.g., by dipping, immersing, spraying, or the like), during which smaller cations in the outer or exterior region of the glass substrate are replaced by, or exchanged with, larger cations of the same valence (usually $1^+$) from the molten salt bath to place the outer or exterior region under compression, while an interior region of the glass (in which no ion exchange occurs) is put under tension. Conditions such as contacting time, molten salt bath temperature, and salt concentration in the molten salt bath can be tailored to achieve a desired DOL and CS in the compressive stress layer (the exterior region in which the ion exchange occurs).

Similarly, the antimicrobial silver-containing region can be formed in a variety of ways, of which chemical diffusion (which optionally can be accompanied by the exchange of another cation out from the glass) of cationic silver from a silver-containing medium (e.g., paste, dispersion, ion exchange bath of molten salts, or the like) is the most common. In general, the glass substrate is contacted with the silver-containing medium (e.g., by dipping, immersing, spraying, or the like), and cationic silver diffuses from the silver-containing medium into an outer or exterior region of the glass substrate. In most situations, however, the cationic silver replaces, or exchanges with, another cations of the same valence (i.e., $1^+$) from the silver-containing medium. Conditions such as contacting time, silver-containing medium temperature, and silver concentration in the silver-containing medium can be tailored to achieve a desired DOR and silver concentration in the silver-containing region (the exterior region in which the cationic silver diffuses or ion exchanges).

By way of example, one exemplary implementation of a method where the compressive stress layer is formed before the antimicrobial silver-containing region entails immersing the glass into a molten $KNO_3$ bath to impart the compressive stress via ion exchange followed by immersing the strengthened glass into an $AgNO_3$-containing molten salt bath to ion exchange $Ag^+$ into the glass.

In such implementations, the $KNO_3$-containing molten salt bath can be formed entirely of $KNO_3$; the $KNO_3$-containing molten salt bath can include $KNO_3$ as the only active component that undergoes ion exchange, as well as additional components that are inactive in the ion exchange process but aid, for example, in molten salt bath stability, pH control, viscosity control, or the like; or the $KNO_3$-containing molten salt bath can include $KNO_3$ and a second or other active component that undergoes ion exchange, and it can optionally include additional components that are inactive in the ion exchange process but aid, for example, in molten salt bath stability, pH control, viscosity control, or the like.

When the $KNO_3$-containing molten salt bath includes a second or other active component that undergoes ion exchange, the second active component can be a so-called "poisoning component" that is present in an amount up to about 10 weight percent (wt %) based on the total weight of the $KNO_3$-containing molten salt bath. As used herein, the term "poisoning component" refers to a salt bath component having a cation (the "poisoning cation") that is both smaller than $K^+$ and that is identical to, or smaller than, the cation originally in the glass substrate that is replaced by, or exchanged with, $K^+$ during the formation of the compressive stress layer. Examples of poisoning components include $NaNO_3$ and $LiNO_3$. The optional poisoning component can be added to the $KNO_3$-containing molten salt bath to enable the presence of the poisoning cation at the surface of the glass substrate after the compressive stress layer-forming step for which the $Ag^+$ will preferentially (i.e., relative to the $K^+$) ion exchange during the subsequent antimicrobial silver-containing region-forming step. That is, the potential for $Ag^+$ for $K^+$ exchange during the subsequent antimicrobial silver-containing region-forming step can be minimized by inclusion of the poisoning component in the $KNO_3$-containing molten salt bath of the compressive stress layer-forming step because the $Ag^+$ will preferentially replace the poisoning cation.

Similarly, in these implementations, the $AgNO_3$-containing molten salt bath can be formed entirely of $AgNO_3$; the $AgNO_3$-containing molten salt bath can include $AgNO_3$ as the only active component that undergoes ion exchange, as well as additional components that are inactive in the ion exchange process but aid, for example, in molten salt bath stability, pH control, viscosity control, or the like; or the $AgNO_3$-containing molten salt bath can include $AgNO_3$ and a second or other active component that undergoes ion exchange, and it can optionally include additional components that are inactive in the ion exchange process but aid, for example, in molten salt bath stability, pH control, viscosity control, or the like.

When the $AgNO_3$-containing molten salt bath includes a second or other active component that undergoes ion exchange, the second active component generally will be $KNO_3$, in a concentration of about 75 wt % to about 99.95 wt %, based on the total weight of the $AgNO_3$-containing molten salt bath. In certain situations, the $AgNO_3$-containing molten salt bath can further include the poisoning component as a third active component (in addition to $KNO_3$ and $AgNO_3$) in an amount that is less than the amount of $AgNO_3$ in the $AgNO_3$-containing molten salt bath and/or less than or equal to the amount of the poisoning component in the $KNO_3$-containing molten salt bath of the compressive stress layer-forming step.

By way of another example, one exemplary implementation of a method where the compressive stress layer is formed after the antimicrobial silver-containing region entails immersing the glass into an $AgNO_3$-containing molten salt bath to ion exchange $Ag^+$ into the glass followed by immersing the Ag-containing glass into a $KNO_3$-containing molten salt bath to impart the compressive stress via ion exchange. The $AgNO_3$-containing molten salt bath and the $KNO_3$-containing molten salt bath can be formed as described above, with the exception of the use of the poisoning component for preferential ion exchange.

By way of still another example, one exemplary implementation of a method where the compressive stress layer and the antimicrobial silver-containing region are formed simultaneously entails immersing the glass into a molten salt bath comprising both $KNO_3$ and $AgNO_3$ to ion exchange $K^+$ and $Ag^+$ into the glass together.

In such implementations, the $KNO_3$— and $AgNO_3$-containing molten salt bath can be formed entirely of $KNO_3$ and $AgNO_3$; the $KNO_3$— and $AgNO_3$-containing molten salt bath can include $KNO_3$ and $AgNO_3$ as the only active components that undergo ion exchange, as well as additional components that are inactive in the ion exchange process but aid, for example, in molten salt bath stability, pH control, viscosity control, or the like; or the $KNO_3$— and $AgNO_3$-containing molten salt bath can include $KNO_3$, $AgNO_3$, and a third or other active component that undergoes ion exchange, and it can optionally include additional components that are inactive in the ion exchange process but aid, for example, in molten salt bath stability, pH control, viscosity control, or the like.

After the compressive stress layer and the antimicrobial silver-containing region are formed, if desired, the optional additional layer(s) can be disposed on the surface of the glass substrate. Depending on the materials chosen, these coatings can be formed using a variety of techniques. For example, the optional additional layer(s) can be fabricated independently using any of the variants of chemical vapor deposition (CVD) (e.g., plasma-enhanced CVD, aerosol-assisted CVD, metal organic CVD, and the like), any of the variants of physical vapor deposition (PVD) (e.g., ion-assisted PVD, pulsed laser deposition, cathodic arc deposition, sputtering, and the like), spray coating, spin-coating, dip-coating, inkjetting, sol-gel processing, or the like. Such processes are known to those skilled in the art to which this disclosure pertains.

It should be noted that between any of the above-described steps or after all of the above-described steps (i.e., providing a glass substrate, forming a compressive stress layer, and an antimicrobial silver-containing region and forming the additional layer on at least a portion of the surface of the substrate), the glass substrate can undergo a treatment in preparation for any of the subsequent steps. As described above, examples of such treatments include physical or chemical cleaning, physical or chemical etching, physical or chemical polishing, annealing, shaping, and/or the like.

By way of example, a chemical cleaning treatment will be desirable after the antimicrobial silver-containing region is formed in situations where the antimicrobial silver-containing region was formed by chemical ion exchange, particularly if the duration of the ion exchange was long, the temperature of the silver-containing medium was high, and/or the silver-containing medium had a high concentration of silver. Under these circumstances, a hazy residue of silver-containing particles (e.g., elemental silver, AgCl, $AgNO_3$, $Ag_2O$, and the like, depending on the composition of the silver-containing medium) can form on the surface of the glass substrate. In some instances haze is especially problematic where higher temperature processes are utilized, substrates are immersed in ion exchange baths including molten salts for longer periods of time, and/or are immersed in ion exchange baths including higher concentrations of silver. FIG. 1 illustrates the presence of haze after groups of substrates are ion exchanged in an ion exchange bath including 0.5 wt % $AgNO_3$ and 95 wt % $KNO_3$ over the course of 42 runs. In FIG. 1, the error bars represent the standard deviation in haze within each run, with each run including 25 glass substrates. The antimicrobial articles evaluated in FIG. 1 were also analyzed using scanning electron microscopy (SEM), transmission electron microscopy (TEM) and grazing incidence x-ray diffraction (GIXRD) analytical techniques to measure the chemical composition of the silver residue found on the antimicrobial glass articles. The results of the SEM, TEM and GIXRD analyses are listed below in Table 1.

TABLE 1

Size and chemistry of silver surface contaminants on antimicrobial glass articles.

| Type of particle | Particle longest cross-sectional dimension | Chemistry |
| --- | --- | --- |
| Clusters | 0.1-100 μm | AgCl |
| Large, dispersed particles | 60-90 μm | $(Ag^0)_n$ or $Ag_2O$ |
| Small, dispersed particles | 30-50 μm | Ag (metal or compound) |

Figure 2:
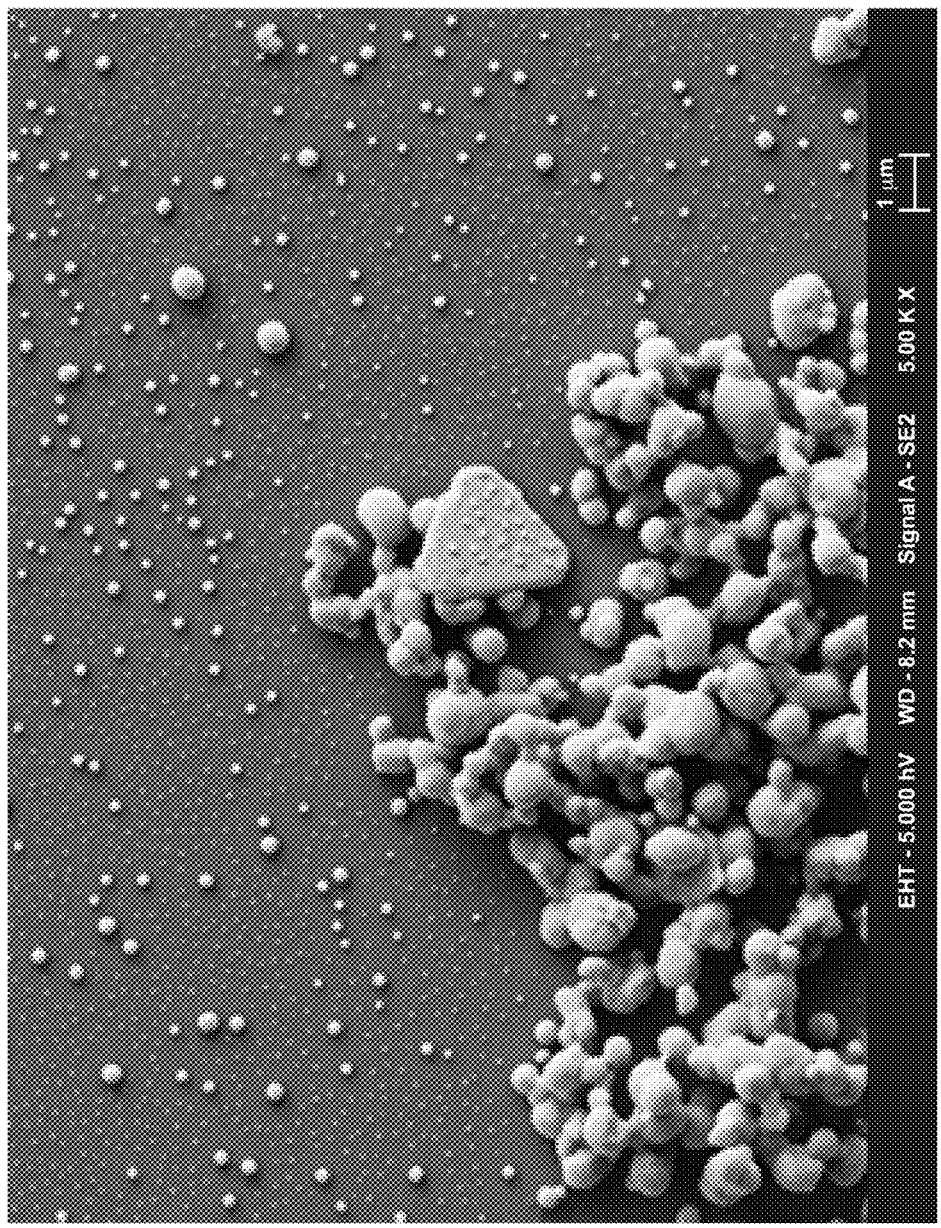
FIG. 2 is a scanning electron microscopy image of an antimicrobial glass article.

FIG. 2 is an SEM image showing silver particles on antimicrobial glass articles, after such articles are washed in water. As shown in FIG. 2, many of the particles had a size of less than about 1 μm. It has been found that haze is primarily caused by particles having a longest cross-sectional dimension of greater than about 1 μm. The term "longest cross-sectional dimension," as used herein, refers to a particular dimension of a convex feature that is parallel to the surface of the substrate. Thus, to clarify, when the convex features are spherical, the longest cross-sectional dimension is the largest diameter of any of the plurality of spherical features; when the convex features are oval-shaped, the longest cross-sectional dimension is the largest diameter of the plurality of the oval-shaped features parallel to the surface of the substrate and along the long axis of the oval; and when the convex features are irregularly-shaped, the longest cross-sectional dimension is the longest line between the two farthest opposing points on a perimeter that is parallel to the surface of the substrate for the plurality of irregularly-shaped features.

Without being bound by theory, it is believed that the adhesion of haze-inducing particles to the surface of the antimicrobial glass articles is generally weak, since haze could be reduced by careful, manual wiping by hand. However, it was found that manual wiping did not remove all of the haze-inducing residue. The removal of haze-inducing residue must be tailored to prevent removal of the silver from the antimicrobial silver-containing layer and/or the alkali ions (e.g., $K^+$) used to form the compressive stress layer. For example, $KNO_3$ and $AgNO_3$ salts are both soluble in water so the use of water-based cleaning should be tailored to prevent removal of such salts from the antimicrobial glass article.

To remove the hazy residue, either a physical or chemical cleaning treatment (or combinations of these treatments) could be implemented. For applications where the surface quality of the final antimicrobial glass article must be high, however, a chemical cleaning treatment will be more appropriate so as to minimize the possibility of forming surface flaws or abrasions. If physical treatments are employed in combination with a chemical treatment, they should be conducted in a particularly gentle approach with minimal durations to minimize the possibility of defect formation in the surface of the antimicrobial glass article.

One such chemical cleaning treatment can involve contacting (e.g., by dipping, immersing, spraying, or the like) the glass substrate having the antimicrobial silver-containing region formed therein with a dilute cleaning solution comprising ammonium hydroxide ($NH_4OH$) and hydrogen peroxide ($H_2O_2$) in water. The concentration of the $NH_4OH$ and/or $H_2O_2$ generally will be less than or equal to about 2 volume percent (vol %), based on the overall volume of the cleaning solution. In some embodiments, the dilute cleaning solution includes about 0.5 vol % ammonium hydroxide and hydrogen peroxide and water (e.g., volume ratio of 1:1:58, $NH_4OH:H_2O_2:H_2O$). Without being bound by theory, it is believed that the combination of ammonium hydroxide and hydrogen peroxide removes both Ag-containing residue and AgCl-containing residue from the surface of the glass substrate. It is also believed that cleaning with this solution advantageously minimizes the loss of ionized Ag, a contributor to the antimicrobial efficacy of the glass substrate.

The dilute cleaning solution of one or more embodiments is about 200× more dilute than standard cleaning solutions and can be used at lower temperatures for shorter periods of time. In one or more embodiments, the contacting step generally can be effected at room or ambient temperatures for a short duration (e.g., less than or equal to about 15 minutes, less than or equal to about 10 minutes, less than or equal to about 6 minutes, or less than or equal to about 5 minutes). It is expected that higher or lower temperatures could reduce or increase, respectively, the required residence time of the cleaning solution, but consideration must also be given to ensuring that no appreciable loss in Ag ions from the glass surface is realized. In some situations, the contacting can be expedited using ultrasonic agitation while the glass substrate is contacted with the cleaning solution. The use of such dilute cleaning solutions, without heating, for such short times results in thorough particulate removal from the surface of the glass substrate, with minimal-to-no cationic silver removal from the glass substrate (i.e., from the antimicrobial silver-containing region). This contacting step can be performed directly after the antimicrobial silver-containing region is formed, or after an initial rinsing step wherein the glass substrate is rinsed of any excess silver-containing medium from the ion exchange step.

Another such chemical cleaning treatment can involve contacting (e.g., by dipping, immersing, spraying, or the like) the glass substrate having the antimicrobial silver-containing region formed therein with a dilute, aqueous cleaning solution comprising a chloride (e.g., sodium chloride). When sodium chloride is the chloride employed in this aqueous cleaning solution, it can range from about 0.01 wt % to about 5 wt %. According to an embodiment, the sodium chloride concentration employed in an aqueous cleaning solution for antimicrobial glass articles can be about 0.01 wt %, 0.05 wt %, 0.1 wt %, 0.5 wt %, 1 wt %, 2 wt %, 3 wt %, 4 wt %, or 5 wt %. Preferably, the aqueous chloride cleaning solution is held at temperatures above ambient during the contacting of the glass substrate. For example, the aqueous chloride cleaning solution can be held at from 30° C. to about 90° C. during the step of contacting the glass substrate.

In an embodiment, the temperature of the aqueous chloride-containing solution is held at about 50° C. to about 70° C. during the contacting of the glass substrate.

Without being bound by theory, it is believed that the free silver ions in the crust left (e.g., as left over on the surface of the glass after $AgNO_3$ immersion) are captured or otherwise bound to the chloride ions ($Cl^-$) in the aqueous chloride cleaning solution to form AgCl. These insoluble particles stay in the rinse solution as precipitates and cannot attach to the antimicrobial glass surface or support further growth of any AgCl or other insoluble Ag-containing compounds present on the surface of the glass. In view of these mechanisms, it is expected that other aqueous cleaning solutions possessing anions that can precipitate silver ions in the solution are also viable as alternatives to a chloride-containing solutions, including but not limited to bromide, iodide, sulfide-, and hydroxide-containing solutions. In general, the bromide-, sulfide- and hydroxide-containing solutions are expected to perform similarly to the chloride-containing solutions, recognizing that solubility of these anions may differ from chloride in water. It is also believed that cleaning with this solution advantageously minimizes the loss of ionized Ag, a contributor to the antimicrobial efficacy of the glass substrate. Another advantage of aqueous cleaning solutions comprising a chloride is that they are generally safe, particularly when the chloride employed in the solution is sodium chloride.

In one or more embodiments, the contacting step employing the aqueous chloride-containing cleaning solution generally can be effected at above-ambient temperatures for a short duration (e.g., less than or equal to about 15 minutes, less than or equal to about 10 minutes, less than or equal to about 6 minutes, or less than or equal to about 5 minutes). It is expected that higher or lower temperatures could reduce or increase, respectively, the required residence time of the chloride-containing cleaning solution, but consideration must also be given to ensuring that no appreciable loss in Ag ions from the glass surface is realized. In some situations, the contacting can be expedited using ultrasonic agitation while the glass substrate is contacted with the aqueous chloride cleaning solution. The use of such cleaning solutions, with minimal heating, for such short times results in thorough particulate removal from the surface of the glass substrate, with minimal-to-no cationic silver removal from the glass substrate (i.e., from the antimicrobial silver-containing region). This contacting step can be performed directly after the antimicrobial silver-containing region is formed, or after an initial rinsing step wherein the glass substrate is rinsed of any excess silver-containing medium from the ion exchange step.

An additional chemical cleaning approach can include contacting (e.g., by dipping, immersing, spraying, or the like) the glass substrate having the antimicrobial silver-containing region formed therein with a dilute, aqueous cleaning solution comprising citric acid. In some implementations, the citric acid can range from about 0.01 wt % to about 5 wt %, preferably between about 0.01 wt % and 1 wt %. According to an embodiment, the citric acid concentration employed in an aqueous cleaning solution for antimicrobial glass articles can be about 0.01 wt %, 0.05 wt %, 0.1 wt %, 0.5 wt %, 1 wt %, 2 wt %, 3 wt %, 4 wt %, or 5 wt %. Preferably, the aqueous, citric acid-containing cleaning solution is held at temperatures above ambient during the contacting of the glass substrate. For example, the aqueous cleaning solution containing citric acid can be held at from 30° C. to about 90° C. during the step of contacting the glass substrate. In an embodiment, the temperature of the aqueous citric acid-containing solution is held at about 50° C. to about 70° C. during the contacting of the glass substrate. In an additional embodiment, the temperature of the aqueous citric acid-containing solution is held at about 50° C. to about 90° C. during the contacting of the glass substrate.

Without being bound by theory, it is believed that the free silver ions in the crust left (e.g., as left over on the surface of the glass after $AgNO_3$ immersion) are stabilized and suspended in the rinse solution by the citric acid. These insoluble, silver-containing particles stay in the rinse solution and cannot attach to the antimicrobial glass surface or support further growth of any AgCl or other insoluble Ag-containing compounds present on the surface of the glass. In view of these mechanisms, it is expected that other aqueous cleaning solutions possessing anion surfactants and/or chelating reagents (e.g., ethylenediamine tetra-acetic acid) that can stabilize silver-containing particles in the solution are also viable as alternatives to citric acid-containing solutions. It is also believed that cleaning with this solution advantageously minimizes the loss of ionized Ag, a contributor to the antimicrobial efficacy of the glass substrate. Another advantage of aqueous cleaning solutions comprising citric acid is that they are generally safe for human handling.

In one or more embodiments, the contacting step employing the aqueous citric acid-containing cleaning solution generally can be effected at above-ambient temperatures for a short duration (e.g., less than or equal to about 15 minutes, less than or equal to about 10 minutes, less than or equal to about 6 minutes, or less than or equal to about 5 minutes). It is expected that higher or lower temperatures could reduce or increase, respectively, the required residence time of the citric acid-containing cleaning solution, but consideration must also be given to ensuring that no appreciable loss in Ag ions from the glass surface is realized. In some situations, the contacting can be expedited using ultrasonic agitation while the glass substrate is contacted with the aqueous, citric acid cleaning solution. The use of such cleaning solutions, with minimal heating, for such short times results in thorough particulate removal from the surface of the glass substrate, with minimal-to-no cationic silver removal from the glass substrate (i.e., from the antimicrobial silver-containing region). This contacting step can be performed directly after the antimicrobial silver-containing region is formed, or after an initial rinsing step wherein the glass substrate is rinsed of any excess silver-containing medium from the ion exchange step.

In some cases, the foregoing chemical cleaning processes can further involve a post-cleaning rinse or wash step where the glass substrate is contacted (e.g., by dipping, immersing, spraying, or the like) with a rinsing agent (e.g., water, a mild detergent, surfactant, or other like solution) and optional brushing (i.e., light mechanical brushing configured to minimize removal of the underlying glass substrate) to fully dislodge or remove any remaining silver-containing particles and/or chemical cleaning solution from the surface of the glass substrate. In one such example, rinsing can involve an immersion step followed by a spray step, wherein the glass substrate is immersed in a deionized water rinsing agent that optionally is ultrasonically agitated for less than or equal to about 3 minutes and then sprayed with a deionized water rinsing agent for less than or equal to about 1 minute. The deionized water rinsing agents optionally can be heated to a temperature of less than or equal to about 60° C. as desired.

According to another implementation, a post-chemical cleaning wash process (hereinafter referred to as a "short DI water wash") for the antimicrobial glass articles can comprise the following steps, all performed between about 65° C. to 75° C.: (a) a rinse shower in DI water for about 10-15 minutes; (b) an immersion in a detergent bath for about 10-15 minutes; (c) a rinse shower in DI water for about 10-15 minutes; (d) a rinse bath using DI water for about 10 to 15 minutes; (e) a bath immersion in DI water for about 10 to 15 minutes; and (f) a hot air dry of about 10 to 15 minutes. This short DI water wash process can assist in the removal of any silver-containing particles on the surface of the antimicrobial glass articles that remain after the chemical cleaning steps (e.g., with aqueous solutions containing ammonium hydroxide/hydrogen peroxide, chlorides or citric acid).

Finally, the chemical cleaning process can further involve a drying step, during which the glass substrate is allowed to dry naturally or exposed to a pressurized stream of air or other gas, which optionally can be heated to a mild temperature (e.g., less than or equal to about 60° C.), to expedite drying.

Once the glass article is formed, it can be used in a variety of applications where the article will come into contact with undesirable microbes. These applications encompass touch-sensitive display screens or cover plates for various electronic devices (e.g., cellular phones, personal data assistants, computers, tablets, global positioning system navigation devices, and the like), non-touch-sensitive components of electronic devices, surfaces of household appliances (e.g., refrigerators, microwave ovens, stovetops, oven, dishwashers, washers, dryers, and the like), medical equipment, biological or medical packaging vessels, and vehicle components, just to name a few devices.

Given the breadth of potential uses for the improved antimicrobial glass articles described herein, it should be understood that the specific features or properties of a particular article will depend on the ultimate application therefor or use thereof. The following description, however, will provide some general considerations.

There is no particular limitation on the average thickness of the glass substrate contemplated herein. In many exemplary applications, however the average thickness will be less than or equal to about 15 millimeters (mm). If the antimicrobial glass article is to be used in applications where it may be desirable to optimize thickness for weight, cost, and strength characteristics (e.g., in electronic devices, or the like), then even thinner substrates (e.g., less than or equal to about 5 mm) can be used. By way of example, if the antimicrobial glass article is intended to function as a cover for a touch screen display, then the substrate can exhibit an average thickness of about 0.02 mm to about 2.0 mm.

While the ultimate limit on the CS and DOL is the avoidance of rendering the glass article frangible, the average DOL of the compressive stress layer generally will be less than about one-third of the thickness of the glass substrate. In most applications, however, the average DOL will be greater than or equal to about 25 μm and less than or equal to about 100 μm. Similarly, the average CS across the depth of the compressive stress layer generally will be between about 200 megapascals (MPa) and about 1.2 gigapascals (GPa). In most applications, the average CS will be greater than 400 MPa.

As stated above, the thickness of the antimicrobial silver-containing region can be limited so as to avoid visible coloration in the glass article and to maximize the antimicrobial efficacy of the cationic silver within the glass substrate. The average thickness of the antimicrobial silver-containing region may be less than the DOL of the compressive stress layer. In some embodiments, as with the DOL of the compressive stress layer, the average thickness of the antimicrobial silver-containing region may be less than about one-third of the thickness of the glass substrate. In some alternative embodiments, the average thickness of the antimicrobial silver-containing region may be up to about 100 micrometers (μm), up to about 150 micrometers (μm), up to about 300 micrometers (μm), or up to the entire thickness of the glass substrate. The exact thickness, however, will vary depending on how the antimicrobial silver-containing region is formed.

For example, if the antimicrobial silver-containing region is formed before or after the compressive stress layer, and both are formed via chemical ion exchange, then the average thickness of the antimicrobial silver-containing region generally may be less than or equal to about 20 micrometers (μm). In many such cases, the average thickness of the antimicrobial silver-containing region may be less than or equal to about 10 micrometers (μm), less than or equal to about 5 micrometers (μm), less than or equal to about 3 micrometers (μm), less than or equal to about 2 micrometers (μm), less than or equal to about 1 micrometers (μm), or less than or equal to about 0.2 micrometers (μm). The minimum average thickness of the antimicrobial silver-containing region may be about 10 nanometers (nm). In some embodiments, the average thickness of the antimicrobial silver-containing region is in the range from about 5 micrometers (μm) to about 8 micrometers (μm) or from about 2 micrometers (μm) to about 5 micrometers (μm). Within this antimicrobial silver-containing region, silver concentrations at the outermost portion of this region (which includes about the outermost 50 nanometers (nm)) of up to about 45 weight percent (wt %), based on the total weight of this portion of the region, can be attained.

In contrast, if the antimicrobial silver-containing region is formed at the same time as the compressive stress layer, and both are formed via chemical ion exchange, then the average thickness of the antimicrobial silver-containing region generally may be up to about 150 micrometers (μm). In some embodiments, the average thickness of the antimicrobial silver-containing region may be in the range from about 20 micrometers (μm) to about 100 micrometers (μm), from about 20 micrometers (μm) to about 150 micrometers (μm) or from about 20 micrometers (μm) to about 300 micrometers (μm). Within this region, silver concentrations at the outermost portion of this region (which includes about the outermost 50 nanometers (nm)) of up to about 10 wt %, 9 wt %, 8 wt %, 7 wt %, 6 wt %, 5 wt %, 4 wt % or 3 wt %, based on the total weight of this portion of the region, can be attained.

When an optional additional layer is used, the average thickness of such a layer will depend on the function it serves. For example if a glare- and/or reflection-resistant layer is implemented, the average thickness of such a layer should be less than or equal to about 200 nanometers (nm). Coatings that have an average thickness greater than this could scatter light in such a manner that defeats the glare and/or reflection resistance properties. Similarly, if a fingerprint- and/or smudge-resistant layer is implemented, the average thickness of such a layer should be less than or equal to about 100 nanometers (nm).

In general, the optical transmittance of the antimicrobial glass article will depend on the type of materials chosen. For example, if a glass substrate is used without any pigments added thereto and/or any optional additional layers are sufficiently thin, the article can have a transparency over the entire visible spectrum of at least about 85%. In certain cases where the antimicrobial glass article is used in the construction of a touch screen for an electronic device, for example, the transparency of the antimicrobial glass article can be at least about 90% over the visible spectrum. In situations where the glass substrate comprises a pigment (or is not colorless by virtue of its material constituents) and/or any optional additional layers are sufficiently thick, the transparency can diminish, even to the point of being opaque across the visible spectrum. Thus, there is no particular limitation on the optical transmittance of the antimicrobial glass article itself.

Regardless of the application or use, the antimicrobial glass articles described herein offer improved discoloration resistance to harsh conditions relative to existing antimicrobial glass articles. As used herein, the term "harsh conditions" refer to elevated temperatures, high relative humidity levels, reactive environments, and/or the like. For example, these can include temperatures of greater than about 180 degrees Celsius (° C.), relative humidity levels of greater than 50 percent (%), reducing environments, and/or the like. Such harsh conditions can be generated during manufacture and/or ordinary use of the antimicrobial glass articles. By way of illustration of the former, harsh conditions can be generated during the formation of any optional additional layers disposed on the surface of the glass substrate (e.g., during polymerization of a fingerprint- and/or smudge-resistant coating on the surface of the glass substrate at elevated temperatures, during direct bonding of adhesives used to adhere the glass substrate to another device, during sputtering of a transparent electrode, during thermal curing of an ink layer, and/or the like), during any intermediate treatment steps (e.g., during plasma cleaning, during chemical etching, during annealing, during chemical cleaning, and/or the like), or the like. Thus, in certain implementations, the antimicrobial glass articles exhibit improved discoloration resistance relative to existing antimicrobial glass articles when exposed to any of the above conditions.

While discoloration resistance can appear to be a qualitative and potentially subjective characterization, there are a number of quantifiable indications of discoloration resistance, examples of which will now be described.

One quantifiable indication of this improved resistance to discoloration can be seen in the change in the optical transmittance that is observed over time. This change can be measured after the formation of the antimicrobial silver-containing region but before the glass article is exposed to any harsh conditions and after the glass article is exposed to harsh conditions. In general, the optical transmittance of the glass articles described herein can be substantially similar both before and after exposure to harsh conditions. In certain implementations, the change in the transmittance of the glass articles described herein after exposure to harsh conditions can be about ±3%. In other implementations, the change in the transmittance of the glass articles described herein after exposure to harsh conditions can be about ±0.5%.

Another quantifiable indication of improved resistance to discoloration is the change in absorbance at about 430 nm, which corresponds to the plasmon resonance associated with the formation of metallic silver nanoparticles (from cationic silver species) in the glass substrate, over time. This change can be measured after the formation of the antimicrobial silver-containing region but before the glass article is exposed to any harsh conditions and after the glass article is exposed to harsh conditions. In general, the absorbance at about 430 nm of the glass articles described herein can be substantially similar both before and after exposure to harsh conditions. In certain implementations, the change in the absorbance at about 430 nm of the glass articles described herein after exposure to harsh conditions can be about ±25%. In other implementations, the change in the absorbance at about 430 nm of the glass articles described herein after exposure to harsh conditions can be about ±10%.

Yet another quantifiable indication of the improved resistance to discoloration is the change in haze that is observed over time. This change can be measured after the formation of the antimicrobial silver-containing region but before the glass article is exposed to any harsh conditions and after the glass article is exposed to harsh conditions. In general, the overall haze of the glass articles described herein after exposure to harsh conditions can be substantially similar to the haze of the as-produced glass articles. In certain implementations, the change in the haze of the glass articles described herein after exposure to harsh conditions can be about ±5%. In other implementations, the change in the haze of the glass articles described herein after exposure to harsh conditions can be about ±2%.

Still another quantifiable indication of the improved resistance to discoloration is the change in CIE 1976 color space coordinates that is observed over time. This change can be measured after the formation of the antimicrobial silver-containing region but before the glass article is exposed to any harsh conditions and after the glass article is exposed to harsh conditions. In general, the individual coordinates (i.e., L*, a*, and b*) of the glass articles described herein after exposure to harsh conditions can be substantially similar to the individual coordinates of the as-produced glass articles. In certain implementations, the change in the L*, a*, and b* coordinates of the glass articles described herein after exposure to harsh conditions can be about ±0.2, ±0.1, and ±0.1, respectively. In other implementations, the change in the L*, a*, and b* coordinates of the glass articles described herein after exposure to harsh conditions can be about ±0.1, ±0.05, and ±0.05, respectively.

The antimicrobial activity and efficacy of the antimicrobial glass articles described herein can be quite high. The antimicrobial activity and efficacy can be measured in accordance with Japanese Industrial Standard JIS Z 2801 (2000), entitled "Antimicrobial Products- Test for Antimicrobial Activity and Efficacy," the contents of which are incorporated herein by reference in their entirety as if fully set forth below. Under the "wet" conditions of this test (i.e., about 37° C. and greater than 90% humidity for about 24 hours), the antimicrobial glass articles described herein can exhibit at least a 5 log reduction in the concentration (or a kill rate of 99.999%) of at least *Staphylococcus aureus, Enterobacter aerogenes*, and *Pseudomonas aeruginosa* bacteria. In certain implementations, the antimicrobial glass articles described herein can exhibit at least a 7 log reduction in the concentration of any bacteria to which it is exposed under these testing conditions.

In scenarios where the wet testing conditions of JIS Z 2801 do not reflect actual use conditions of the antimicrobial glass articles described herein (e.g., when the glass articles are used in electronic devices, or the like), the antimicrobial activity and efficacy can be measured with the JIS Z 2801 (2000) protocol under a set of modified, "drier" conditions, hereinafter referred to as a "modified JIS Z 2801 test". For example, the glass articles can be tested between about 23 and about 37° C. and at about 38 to about 42% humidity for about 24 hours. Specifically, 5 control samples and 5 test samples can be used, wherein each sample has a specific inoculum composition and volume applied thereto, with a sterile coverslip applied to the inoculated samples to ensure uniform spreading on a known surface area. The covered samples can be incubated under the conditions described above, dried for about 6 to about 24 hours, rinsed with a buffer solution, and enumerated by culturing on an agar plate, the last two steps of which are similar to the procedure employed in the standard JIS Z 2801 test. Using this test, the antimicrobial glass articles described herein can exhibit at least a 1 log reduction in the concentration (or a kill rate of 90%) of at least *Staphylococcus aureus* bacteria and at least a 2 log reduction in the concentration (or a kill rate of 99.99%) of at least *Enterobacter aerogenes*, and *Pseudomonas aeruginosa* bacteria. In certain implementations, the antimicrobial glass articles described herein can exhibit at least a 3 log reduction in the concentration of any bacteria to which it is exposed under these testing conditions.

In other scenarios where the wet testing conditions of JIS Z 2801 and/or the modified JIS Z 2801 test do not reflect actual use conditions of the antimicrobial glass articles described herein (e.g., when the glass articles are used in electronic devices, or the like), the antimicrobial activity and efficacy can be measured using "dry" conditions modeled upon an U.S. EPA test protocol for assessing the antimicrobial efficacy of Cu-containing surfaces. These conditions described herein are collectively referred to herein as "Dry Test" or "modified EPA Test" conditions. The antimicrobial glass articles may exhibit at least a 1 log reduction in the concentration (or a kill rate of 90%) or even at least a 2 log reduction in the concentration (or kill rate of 99%) of at least *Staphylococcus aureus*, *Enterobacter aerogenes*, and *Pseudomonas aeruginosa* bacteria when tested under the Dry Test (also referred to as the "modified EPA Test"), which is described in U.S. Provisional Patent Application No. 61/908,401, and hereby incorporated by reference in its entirety as if fully set forth below. In a specific embodiment that might be particularly advantageous for applications such as touch accessed or operated electronic devices, an antimicrobial glass article is formed from a chemically strengthened (ion exchanged) alkali aluminosilicate flat glass sheet. The average thickness of the glass sheet is less than or equal to about 1 mm, the average DOL of the ion exchanged compressive stress layer on each major surface of the glass sheet will be about 40 micrometers ($\mu$m) to about 100 micrometers ($\mu$m), and the average CS across the depth of the compressive stress layer on each major surface will be about 400 MPa to about 1.1 GPa. The average thickness of the antimicrobial silver-containing region, which is formed by a second ion exchange step that occurs after compressive stress layer is formed, will be about 500 nanometers (nm) to about 10 micrometers ($\mu$m). A silver concentration of about 30 wt % to about 40 wt % can be attained in the outermost (i.e., closest to the glass substrate surface) 50 nm of the antimicrobial silver-containing region, based on the total weight of this portion of the antimicrobial silver-containing region. This antimicrobial glass article can have an initial optical transmittance of at least about 90% across the visible spectrum and a haze of less than 1%.

In certain cases, one of the major surfaces of the glass sheet can have an anti-reflection coating and/or an anti-fingerprint coating disposed thereon. After deposition of the anti-reflection coating and/or the anti-fingerprint coating (which can involve temperatures of greater than 1800° C., relative humidity levels of greater than 50%, and exposure to plasma cleaning steps before and/or after deposition), the antimicrobial glass article can have an optical transmittance of at least about 90% across the visible spectrum and a haze of less than 1%. In addition, the change in the L*, a*, and b* coordinates of the glass article after deposition of the anti-reflection coating and/or the anti-fingerprint coating (relative to the uncoated article) can be less than about ±0.15, ±0.08, and ±0.08, respectively. Such an antimicrobial glass article can be used in the fabrication of a touch screen display for an electronic device, offering desirable strength, optical properties, antimicrobial behavior, and resistance to discoloration. In addition, such an antimicrobial glass article can exhibit at least a 5 log reduction in the concentration any bacteria to which it is exposed under the testing conditions of JIS Z 2801.

In another specific embodiment that might be particularly advantageous for applications such as touch accessed or operated electronic devices, an antimicrobial glass article is formed from a chemically strengthened (ion exchanged) alkali aluminosilicate flat glass sheet. The average thickness of the glass sheet is less than or equal to about 1 mm, the average DOL of the ion exchanged compressive stress layer on each major surface of the glass sheet will be about 40 micrometers ($\mu$m) to about 100 micrometers ($\mu$m), and the average CS across the depth of the compressive stress layer on each major surface will be about 500 MPa to about 1.2 GPa. The average thickness of the antimicrobial silver-containing region, which is formed at the same time that the compressive stress layer is formed (e.g., by including about 0.1 wt % to about 1 wt % AgNO$_3$ in the chemical strengthening molten salt bath), will be about 25 micrometers ($\mu$m) to about 110 micrometers ($\mu$m). A silver concentration of about 1 wt % to about 5 wt % can be attained in the outermost (i.e., closest to the glass substrate surface) 50 nm of the antimicrobial silver-containing region, based on the total weight of this portion of the antimicrobial silver-containing region. This antimicrobial glass article can have an initial optical transmittance of at least about 90% across the visible spectrum and a haze of less than 1%.

In certain cases, one of the major surfaces of the glass sheet can have an anti-reflection coating and/or an anti-fingerprint coating disposed thereon. After deposition of the anti-reflection coating and/or the anti-fingerprint coating (which can involve temperatures of greater than 180° C., relative humidity levels of greater than 50%, and exposure to plasma cleaning steps before and/or after deposition), the antimicrobial glass article can have an optical transmittance of at least about 90% across the visible spectrum and a haze of less than 1%. In addition, the change in the L*, a*, and b* coordinates of the glass article after deposition of the anti-reflection coating and/or the anti-fingerprint coating (relative to the uncoated article) can be less than about ±0.1, ±0.06, and ±0.06, respectively. Such an antimicrobial glass article can be used in the fabrication of a touch screen display for an electronic device, offering desirable strength, optical properties, antimicrobial behavior, and resistance to discoloration. In addition, such an antimicrobial glass article can exhibit at least a 5 log reduction in the concentration any bacteria to which it is exposed under the testing conditions of JIS Z 2801.

Various embodiments will be further clarified by the following examples.

EXAMPLE 1

Comparative Examples 1A-1C, Examples 2A-2D, 3A-3E and Comparative Example 4A were prepared by providing glass substrates with the nominal composition of about 57.50 mol % SiO$_2$, about 16.48 mol % Al$_2$O$_3$, 16.71 mol % Na$_2$O, 2.79 mol % MgO, about 0.05 mol % SnO$_2$, and about 6.46 mol % P$_2$O$_5$. The glass substrates had dimensions of 1"×1"×0.5 mm and were first immersed in a first ion exchange bath including $KNO_3$ molten salt at a temperature of about 390° C. for 2.5 hours each to provide strengthened glass substrates. The strengthened glass substrates were then immersed in a second ion exchange bath including either 0.25 wt % $AgNO_3$ or 0.5 wt % $AgNO_3$, along with a balance of $KNO_3$. All of the strengthened glass substrates were immersed in the second bath for the same period of time and temperature to form antimicrobial glass articles, at 390° C. for 1 hour. Thereafter, the antimicrobial glass articles were subjected to one of the cleaning conditions listed in Table 2. The phrase "dilute cleaning solution" has been abbreviated to "DCS" in Table 2 below and refers to a solution according to one or more embodiments, comprising ammonium hydroxide ($NH_4OH$) and hydrogen peroxide ($H_2O_2$) in water. Further, the phrase "deionized water" has been abbreviated to "DI" in Table 2 below.

TABLE 2

Cleaning Conditions for Comparative Examples 1A-1C, Examples 2A-2D, Examples 3A-3E and Comparative Example 4A.

| Ex. | wt. % $AgNO_3$ in $2^{nd}$ bath | Condition | Step 1 | Step 2 | Step 3 | Step 4 | Spray |
|---|---|---|---|---|---|---|---|
| Comp. 1A | 0.5 | Water only | 3 min., 70° C. DI water (3 L) | 10 sec., 22° C. DI water (3 L) | — | — | 10 sec., 22° C. DI water |
| Comp. 1B | 0.5 | Water only | 6 min., 70° C. DI water (3 L) | 10 sec., 22° C. DI water (3 L) | — | — | 10 sec., 22° C. DI water |
| Comp. 1C | 0.5 | Water only | 12 min., 70° C. DI water (3 L) | 10 sec., 22° C. DI water (3 L) | — | — | 10 sec., 22° C. DI water |
| 2A | 0.5 | Dilute cleaning solution, then water | 6 min., 22° C., DCS(9 L) | 10 sec., 22° C. DI water (3 L) | — | — | 10 sec., 22° C. DI water |
| 2B | 0.25 | Dilute cleaning solution, then water | 6 min., 22° C., DCS(9 L) | 10 sec., 22° C. DI water (3 L) | — | — | 10 sec., 22° C. DI water |
| 2C | 0.5 | Dilute cleaning solution, then water | 12 min., 22° C., DCS(9 L) | 10 sec., 22° C. DI water (3 L) | — | — | 10 sec., 22° C. DI water |
| 2D | 0.5 | Dilute cleaning solution, then water | 24 min., 22° C., DCS(9 L) | 10 sec., 22° C. DI water (3 L) | — | — | 10 sec., 22° C. DI water |
| 3A | 0.5 | Water, then dilute cleaning solution | 3 min., 70° C. DI water (3 L) | 6 min. 22° C., DCS(9 L) | 10 sec., 22° C. DI water (3 L) | — | 10 sec., 22° C. DI water |
| 3B | 0.25 | Water, then dilute cleaning solution | 3 min., 70° C. DI water (3 L) | 6 min. 22° C., DCS(9 L) | 10 sec., 22° C. DI water (3 L) | — | 10 sec., 22° C. DI water |
| 3C | 0.5 | Water, then dilute cleaning solution | 3 min., 70° C. DI water (3 L) | 6 min. 22° C., DCS(9 L) | 10 sec., 22° C. DI water (3 L) | — | 10 sec., 22° C. DI water |
| 3D | 0.5 | Water, then dilute cleaning solution | 2 min., 70° C. DI water (3 L) | 2 min. 50° C., DCS(8.4 L) | 2 min., 22° C. DI water (3 L) | 6 min., 22° C. DCS(8.4 L) | 10 sec., 22° C. DI water |
| 3E | 0.5 | Water, then dilute cleaning solution | 10 min., 70° C. DI water (3 L) | 10 min., 50° C. DI water (3 L) | 10 sec., 22° C. DI water (3 L) | 6 min., 22° C. DCS(8.4 L) | 10 sec., 22° C. DI water |
| Comp. 4A | 0.5 | Water, then scrubbing | 3 min., 70° C. DI water (3 L) | 10 sec., 22° C. DI water & Sponge | — | — | 10 sec., 22° C. DI water |

Table 3 below lists the average haze values for Comparative Examples 1A-1C, Examples 2A-2D, Examples 3A-3E and Comparative Example 4A.

TABLE 3

Haze values for Comparative Examples 1A-1C, Examples 2A-2D, Examples 3A-3E and Comparative Example 4A.

| Ex. | wt. % AgNO$_3$ in 2$^{nd}$ bath | Condition | Total contact time (min) | Average % Haze | Stdev |
|---|---|---|---|---|---|
| Comp. 1A | 0.5 | Water only | 3 | 0.49 | 0.688 |
| Comp. 1B | 0.5 | Water only | 6 | 0.09 | 0.032 |
| Comp. 1C | 0.5 | Water only | 12 | 0.13 | 0.071 |
| 2A | 0.5 | Dilute cleaning solution, then water | 6 | 0.05 | 0.018 |
| 2B | 0.25 | Dilute cleaning solution, then water | 6 | 0.0 | 0.008 |
| 2C | 0.5 | Dilute cleaning solution, then water | 12 | 0.05 | 0.025 |
| 2D | 0.5 | Dilute cleaning solution, then water | 24 | 0.04 | 0.006 |
| 3A | 0.5 | Water, then dilute cleaning solution | 9 | 0.05 | 0.015 |
| 3B | 0.25 | Water, then dilute cleaning solution | 9 | 0.00 | 0.011 |
| 3C | 0.5 | Water, then dilute cleaning solution | 9 | 0.03 | 0.016 |
| 3D | 0.5 | Water, then dilute cleaning solution | 12 | 0.06 | 0.027 |
| 3E | 0.5 | Water, then dilute cleaning solution | 36 | 0.03 | 0.024 |
| Comp. 4A | 0.5 | Water, then scrubbing | 3 | 0.11 | 0.072 |

Figure 3:
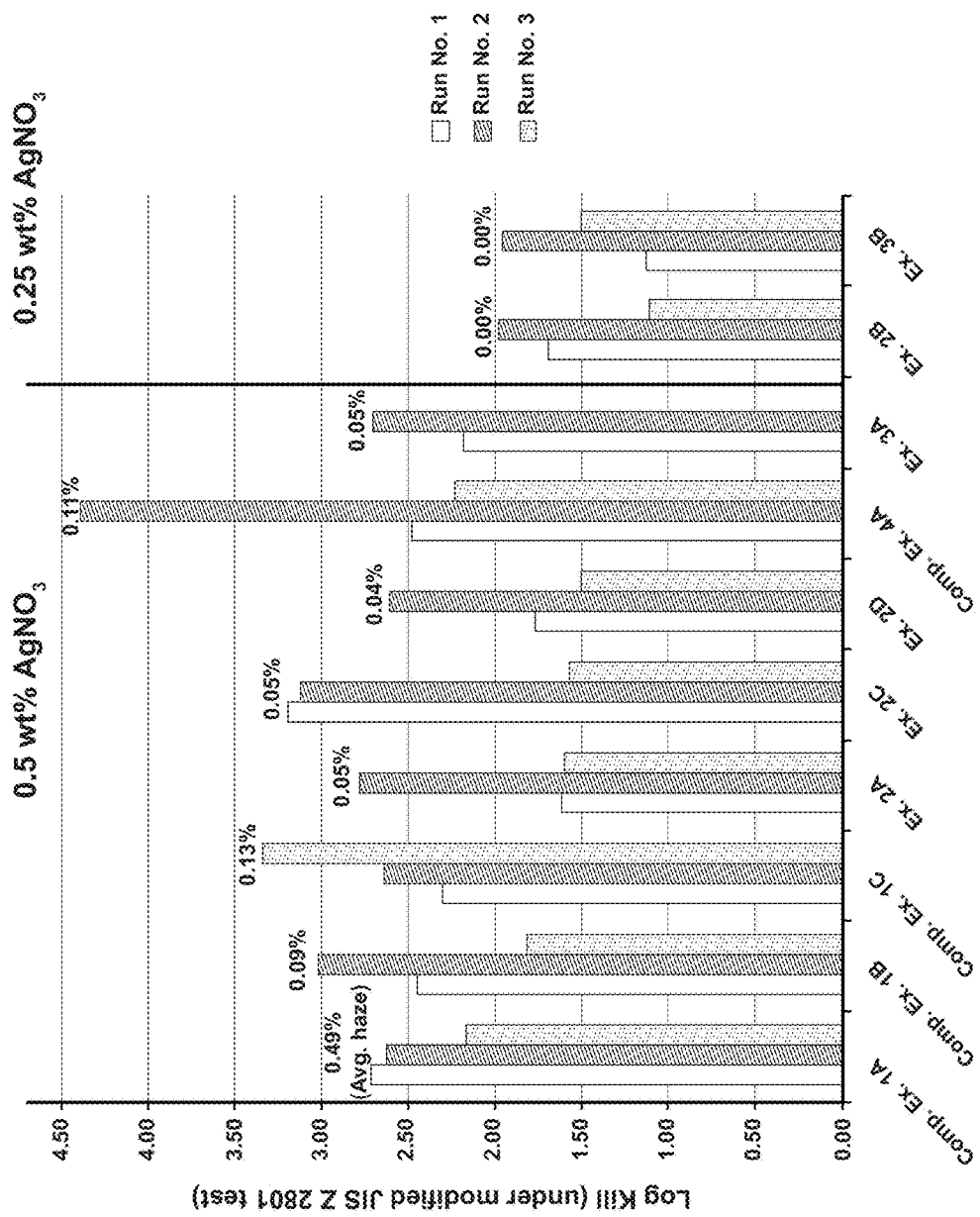
FIG. 3 is a graph showing the antimicrobial efficacy of Comparative Examples 1A-1C, Examples 2A-2D, 3A-3B and Comparative Example 4A, antimicrobial glass articles subjected to various cleaning conditions according to one or more embodiments.
Figure 4:
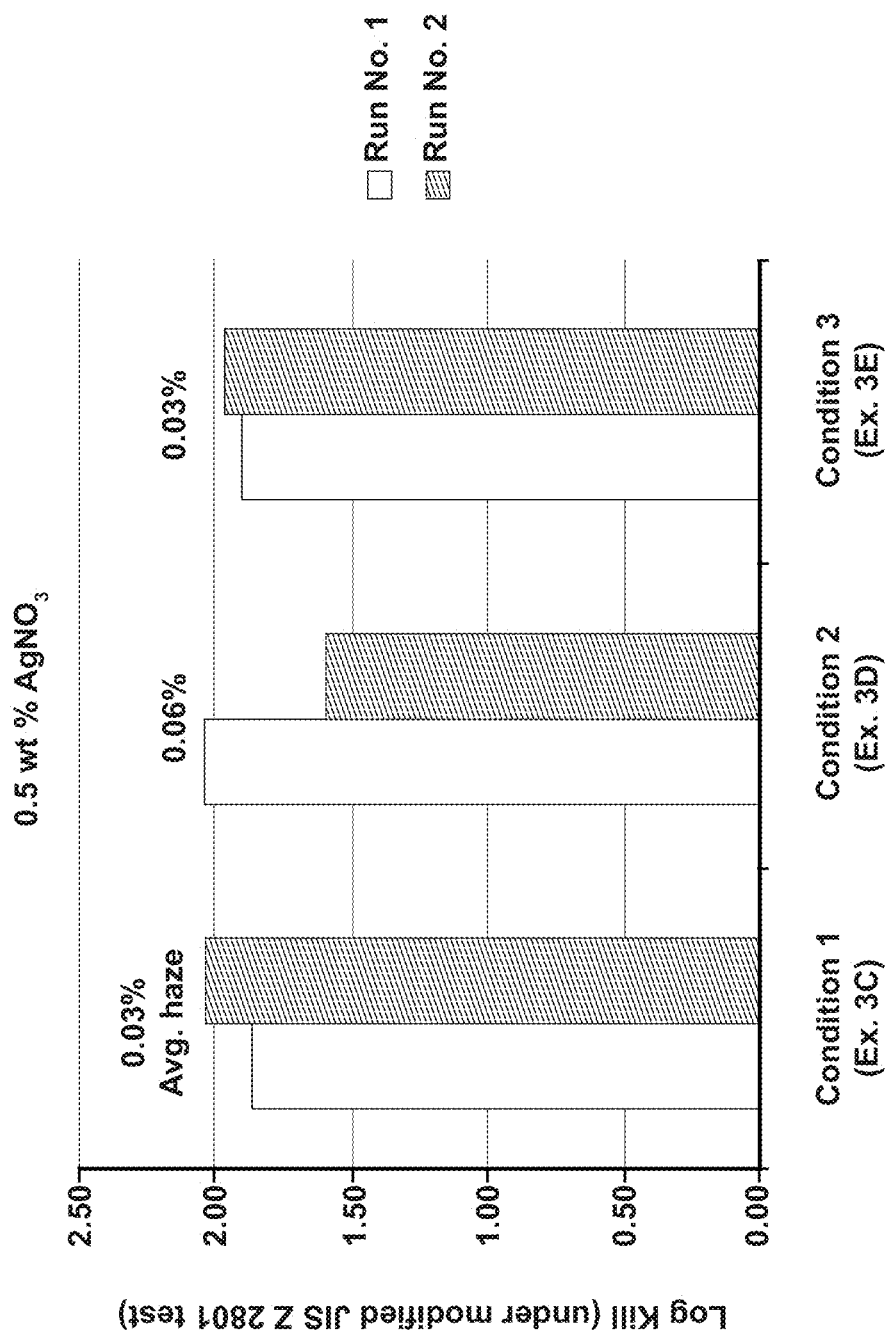
FIG. 4 is a graph showing the antimicrobial efficacy of Examples 3C, 3D and 3E, antimicrobial glass articles subjected to various cleaning conditions according to one or more embodiments.

The antimicrobial articles according to Comparative Examples 1A-1C, Examples 2A-2D, Examples 3A-3E and Comparative Example 4A were then subjected to antimicrobial efficacy testing under the modified JIS Z 2801 (2000) testing conditions, with the results depicted in FIGS. 3-4. In FIG. 3, the results from antimicrobial efficacy testing for all of the Examples except for Examples 3C, 3D and 3E have been illustrated. Three separate antimicrobial testing runs were performed for each Example. In particular, FIG. 3 shows that the Examples with 0.5 wt. % AgNO$_3$ exhibited antimicrobial efficacy indicative of about 2-3 log kill on average. Haze levels were also reduced for the Examples that employed the "dilute cleaning solution, then water" treatment (e.g., Ex. 2A) compared to the Examples subjected to the "water only" treatment (e.g., Comp. Ex. 1A). The Examples with 0.25 wt. % AgNO$_3$ (i.e., Ex. 2B and Ex. 3B) exhibited the least amount of haze, but did not perform as well with respect to antimicrobial efficacy, averaging about 1.5-1.7 log kill.

FIG. 4 illustrates antimicrobial efficacy levels, under the modified JIS Z 2801 (2000) testing conditions, when the cleaning condition "water, then dilute cleaning solution" is performed at 9 minutes ("condition 1"), 12 minutes ("condition 2") and 36 minutes ("condition 3") on antimicrobial glass articles with 0.5 wt. % Ag NO$_3$ (i.e., the conditions for Examples 3C, 3D and 3E, respectively). Two antimicrobial efficacy testing runs were performed for each Example. In particular, FIG. 4 illustrates that there is no significant change to the antimicrobial efficacy when the "water, then dilute cleaning solution" treatment described herein is utilized for 9, 12 and 36 minutes of immersion time. However, as shown in FIG. 4, there is improvement in haze when the cleaning treatment described herein is utilized. As such, the results in FIGS. 3 and 4 show that both the "dilute cleaning solution, then water" and "water, then dilute cleaning solution" treatments can reduce haze levels without negatively impacting antimicrobial efficacy.

Figure 5:
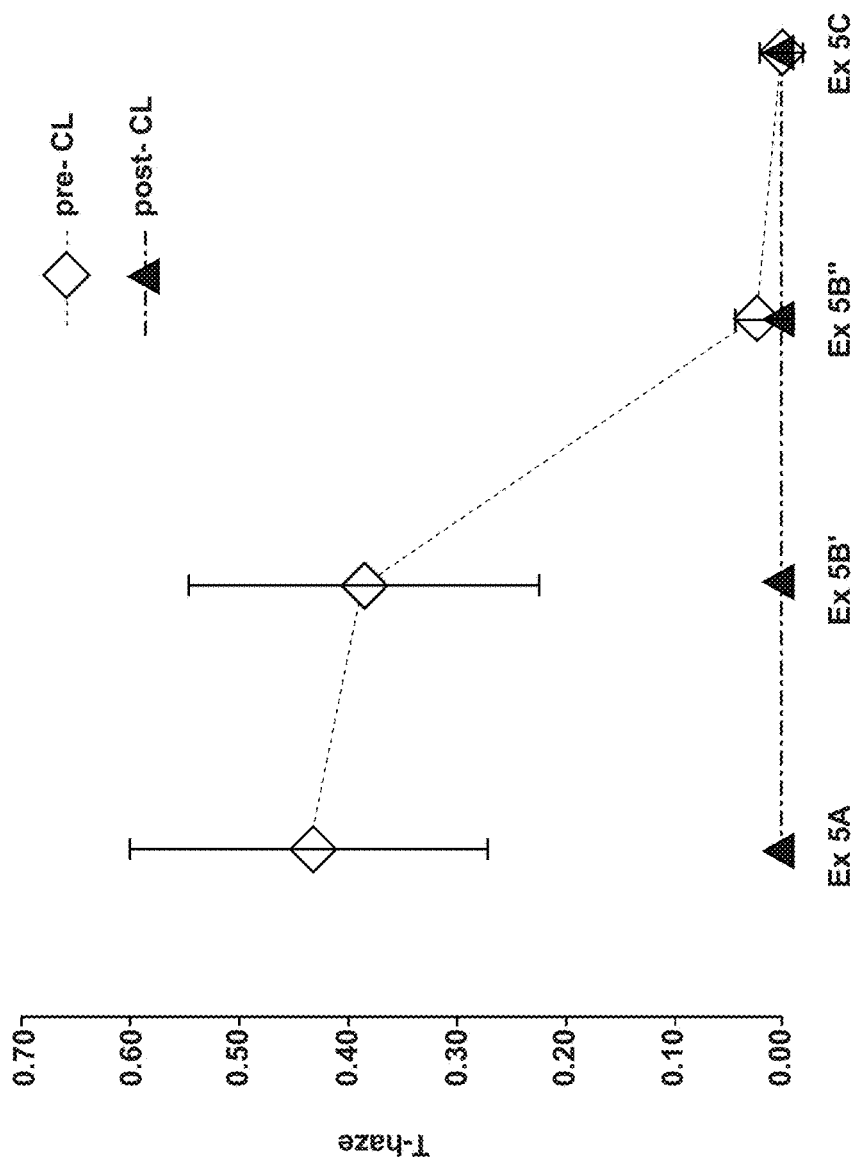
FIG. 5 is a graph showing transmittance haze values for antimicrobial glass articles subjected to water-, chloride-, citric acid- and ammonium hydroxide/hydrogen peroxide-based cleaning solutions according to one or more embodiments.

FIG. 5 illustrates transmittance haze values for antimicrobial glass articles subjected to water-, chloride-, citric acid- and ammonium hydroxide/hydrogen peroxide-based cleaning solutions according to one or more embodiments. Examples 5A, 5B', 5B" and 5C correspond to antimicrobial glass substrates cleaned with (a) 70° C. DI water for 5 minutes, (b) a 70° C. aqueous solution containing NaCl at 0.1 wt % for 5 minutes, (c) a 70° C. aqueous solution containing citric acid at 0.1 wt % for 5 minutes, and (d) a 70° C. dilute aqueous solution containing ammonium hydroxide and hydrogen peroxide ("A/P") for 5 minutes, respectively. All of the antimicrobial glass substrates employed in Examples 5A, 5B', 5B" and 5C were fabricated with 0.4 wt % AgNO$_3$ at 390° C. for 1 hour. After the chemical cleaning steps, the samples were further subjected to an additional short, DI water wash.

As shown in FIG. 5, transmittance-haze measurement values were obtained from Examples 5A, 5B', 5B" and 5C after the chemical cleaning step (denoted by "pre-CL," hollow diamond symbols in FIG. 5) and again after the short, DI water wash (denoted by "post-CL," solid triangle symbols in FIG. 5). As demonstrated by FIG. 5, all of the cleaning processes, including hot DI water (i.e., Ex. 5A) and NaCl-containing solution (i.e., Ex. 5B'), effectively reduce the transmittance-haze values to about zero when coupled with the additional short, DI water wash. It should be noted that low levels of haze can still be observed in the Examples 5A and 5B' through low magnification optical microscopy even after the short, DI water wash.

Referring again to FIG. 5, the citric-acid containing and A/P-containing cleaning solutions (Examples 5B" and 5C, respectively) also effectively removed haze without the need for the additional short, DI water wash. In addition, appreciable amounts of haze cannot be observed in Examples 5B" and 5C after completion of the short, DI water wash.

Figure 6:
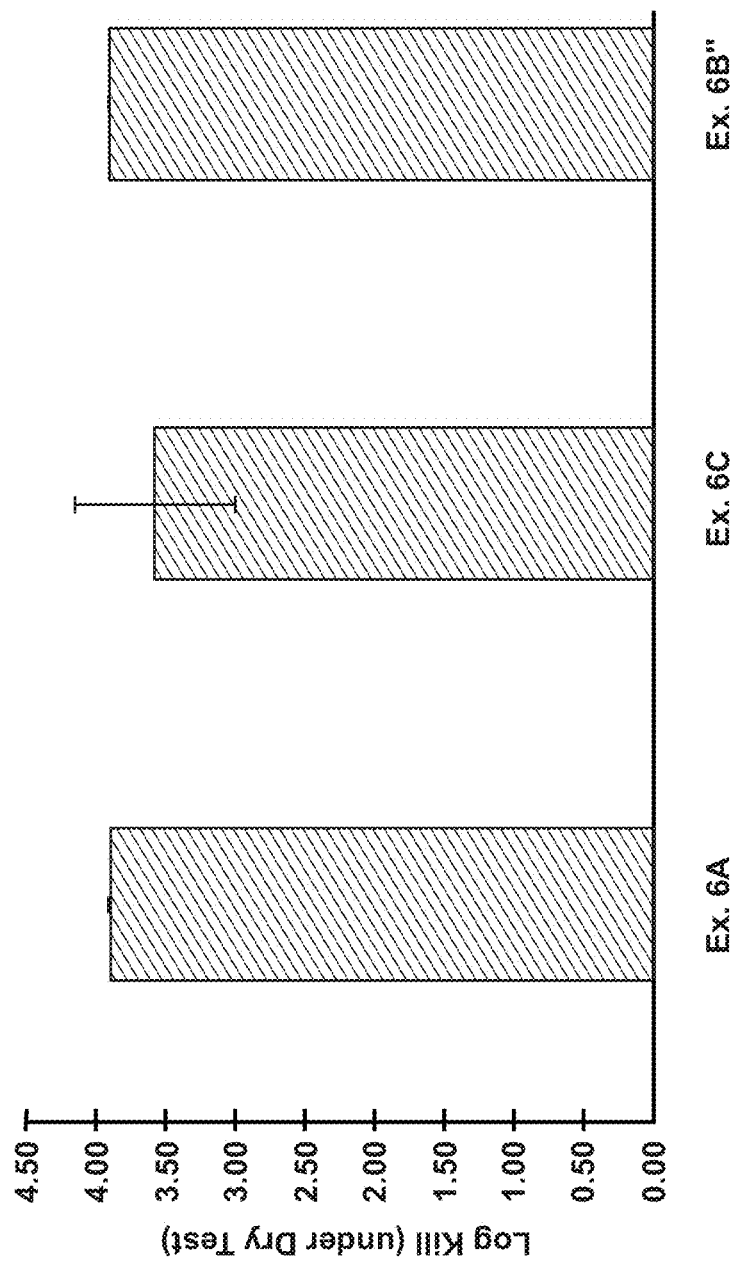
FIG. 6 is a graph showing the antimicrobial efficacy of Comparative Example 6A, and Example 6B" and 6C, antimicrobial glass articles subjected to various cleaning conditions according to one or more embodiments.
Figure 7:
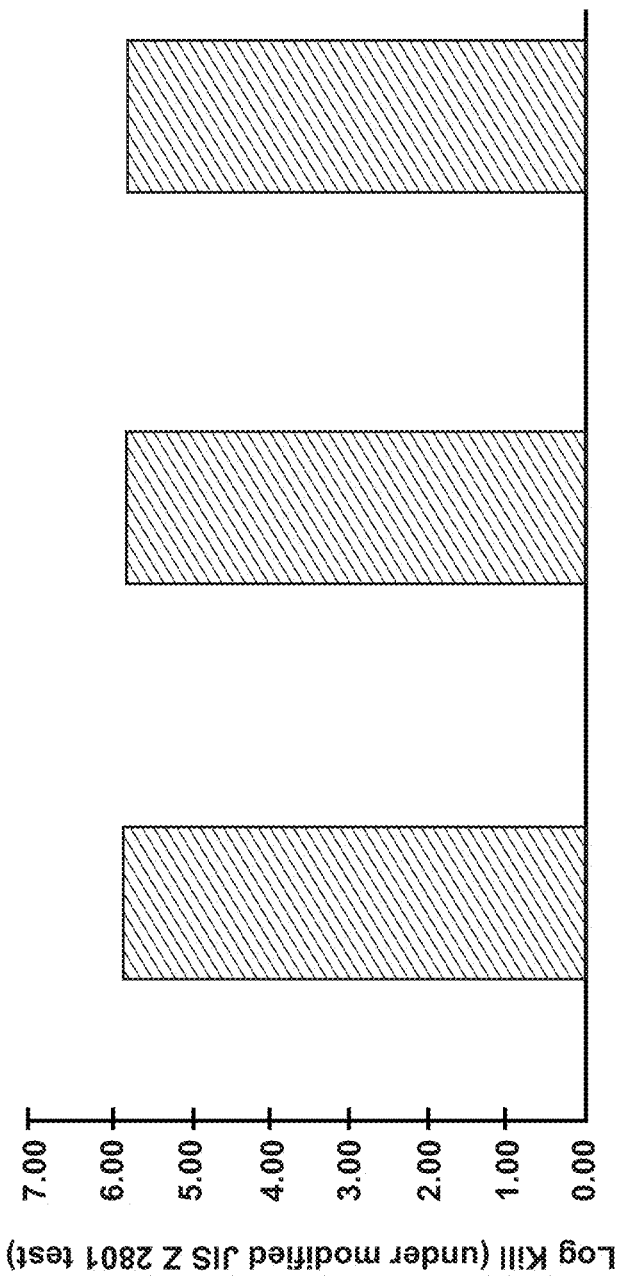
FIG. 7 is a graph showing the antimicrobial efficacy of Comparative Example 7A, and Examples 7B" and 7C, antimicrobial glass articles subjected to various cleaning conditions according to one or more embodiments.

In FIGS. 6-7, antimicrobial glass substrates fabricated with a 0.4 wt % AgNO$_3$ bath and cleaned according to the Example 5B" and 5C conditions with citric acid-containing and A/P-containing aqueous solutions, respectively, were subjected to antimicrobial efficacy testing. These samples were also subjected to a post-cleaning rinse in DI water (i.e., a short, DI water wash") and are identified as Examples 6B" and 6C in FIG. 6 and Examples 7B" and 7C in FIG. 7, respectively. In addition, a control group of antimicrobial glass samples was fabricated with a 0.5 wt % AgNO$_3$ bath and cleaned with an A/P-containing solution (not cleaned with a final, short DI water wash) and subjected to antimicrobial efficacy testing. These control samples are identified as Examples 6A and 7A in FIGS. 6-7, respectively.

The results depicted in FIG. 6 correspond to antimicrobial efficacy testing using the Dry Test and demonstrate log kill values approaching 4 for Examples 6B" and 6C, comparable to the control group Example 6A. The results depicted in FIG. 7 correspond to antimicrobial efficacy testing using the modified JIS Z 2801 test and demonstrate log kill values approaching 6 for Examples 7B" and 7C, again comparable to the control group Example 7A. In sum, the antimicrobial glass samples cleaned with both the A/P and citric acid-containing solutions and a post-cleaning DI water wash to remove haze demonstrated high antimicrobial efficacy levels consistent with control antimicrobial glass articles cleaned with an A/P-containing solution, but not subjected to a post-cleaning DI water wash.

While the embodiments disclosed herein have been set forth for the purpose of illustration, the foregoing description should not be deemed to be a limitation on the scope of the disclosure or the appended claims. Accordingly, various modifications, adaptations, and alternatives may occur to one skilled in the art without departing from the spirit and scope of the present disclosure or the appended claims.

What is claimed is:

1. A method of making an antimicrobial glass article, the method comprising:
   providing a glass substrate;
   forming a compressive stress layer that extends inward from a surface of the glass substrate to a first depth;
   forming an antimicrobial ionic silver-containing region that extends inward from the surface of the glass substrate to a second depth, the surface of the glass substrate containing a haze-inducing residue containing ionic silver; and
   chemically cleaning the glass substrate after the forming steps by contacting the glass substrate with a cleaning solution at an ambient temperature for less than or equal to about 15 minutes to remove the haze-inducing residue containing ionic silver from the surface of the glass substrate, wherein the cleaning solution comprises any one of:
   ammonium hydroxide and hydrogen peroxide in water;
   about 0.01 wt % to about 5 wt % sodium chloride in water, and
   about 0.01 wt % to about 5 wt % citric acid in water.

2. The method of claim 1, further comprising:
   contacting the glass substrate with a rinsing agent after the step of chemically cleaning the glass substrate.

3. The method of claim 2, wherein the step of contacting the glass substrate with a rinsing agent comprises:
   immersing the glass substrate in the rinsing agent; and
   spraying the glass substrate with the rinsing agent after the immersing.

4. The method of claim 1, wherein the second depth is less than the first depth, and the glass substrate comprises a low concentration of nonbridging oxygens.

5. The method of claim 1, wherein the antimicrobial ionic silver-containing region comprises a silver concentration of about 5 weight percent or greater, based on the total weight of the antimicrobial silver-containing region.

6. The method of claim 1, further comprising:
   forming an additional layer on at least a portion of the surface of the substrate, wherein the additional layer comprises a reflection-resistant coating, a glare-resistant coating, fingerprint-resistant coating, smudge-resistant coating, a color-providing composition, an environmental barrier coating, or an electrically conductive coating.

7. The method of claim 4, wherein the concentration of nonbridging oxygens in the glass substrate is in the range from about −1 mol % to about 20 mol %.

8. The method of claim 1, wherein a compressive stress of the compressive stress layer is about 200 megapascals to about 1.2 gigapascals and the first depth is less than about 100 micrometers ($\mu m$), and the antimicrobial ionic silver-containing region has an average thickness of less than or equal to about 20 micrometers ($\mu m$).

9. The method of claim 8, wherein a silver concentration at an outermost 50 nanometers (nm) of the antimicrobial ionic silver-containing region is up to about 45 weight percent, based on a total weight of the outermost 50 nanometers (nm) of the antimicrobial ionic silver-containing region.

10. The method of claim 1, wherein a compressive stress of the compressive stress layer is about 200 megapascals to about 1.2 gigapascals and the first depth is less than about 100 micrometers ($\mu m$), and the antimicrobial ionic silver-containing region has an average thickness of up to about 150 micrometers ($\mu m$).

11. The method of claim 1, wherein ammonium hydroxide and hydrogen peroxide in water are each present in an amount of less than 2 volume percent.

12. The method of claim 1, wherein contacting the glass substrate with a cleaning solution includes using ultrasonic agitation while the glass substrate is contacted with the cleaning solution.

13. The method of claim 1, wherein the cleaning solution comprises any one of:
   about 0.01 wt % to about 5 wt % sodium chloride in water; and
   about 0.01 wt % to about 5 wt % citric acid in water.

14. The method of claim 1, wherein the cleaning solution comprises about 0.01 wt % to about 5 wt % sodium chloride in water.

15. The method of claim 1, wherein the cleaning solution comprises about 0.01 wt % to about 5 wt % citric acid in water.

16. A method of making an antimicrobial glass article, the method comprising:
   providing a glass substrate;
   forming a compressive stress layer that extends inward from a surface of the glass substrate to a first depth;
   forming an antimicrobial ionic silver-containing region that extends inward from the surface of the glass substrate to a second depth, the surface of the glass substrate containing a haze-inducing residue containing ionic silver; and
   chemically cleaning the glass substrate after the forming steps by contacting the glass substrate with a chemical cleaning solution to remove the haze-inducing residue containing ionic silver from the surface of the glass substrate and to form an antimicrobial glass article exhibiting an average haze of about 0.1% or less.

17. The method of claim 16, wherein the chemical cleaning solution comprises any one of:
   ammonium hydroxide and hydrogen peroxide in water;
   about 0.01 wt % to about 5 wt % sodium chloride in water, and
   about 0.01 wt % to about 5 wt % citric acid in water.

18. The method of claim 17, wherein ammonium hydroxide and hydrogen peroxide in water are each present in an amount of less than 2 volume percent.

19. The method of claim 16, further comprising:
   contacting the glass substrate with a rinsing agent after the step of chemically cleaning the glass substrate.

20. The method of claim 19, wherein the step of contacting the glass substrate with a rinsing agent comprises:
   immersing the glass substrate in the rinsing agent; and
   spraying the glass substrate with the rinsing agent after the immersing.

21. The method of claim 16, wherein contacting the glass substrate with a chemical cleaning solution comprises a contact time of less than or equal to about 15 minutes.

22. The method of claim 16, wherein contacting the glass substrate with a cleaning solution includes using ultrasonic agitation while the glass substrate is contacted with the cleaning solution.

23. The method of claim 16, wherein the cleaning solution comprises any one of:

about 0.01 wt % to about 5 wt % sodium chloride in water; and about 0.01 wt % to about 5 wt % citric acid in water.

24. The method of claim 16, wherein the cleaning solution comprises about 0.01 wt % to about 5 wt % sodium chloride in water.

25. The method of claim 16, wherein the cleaning solution comprises about 0.01 wt % to about 5 wt % citric acid in water.

* * * * *

UNITED STATES PATENT AND TRADEMARK OFFICE
CERTIFICATE OF CORRECTION

PATENT NO. : 10,131,574 B2
APPLICATION NO. : 14/306317
DATED : November 20, 2018
INVENTOR(S) : Yuhui Jin et al.

It is certified that error appears in the above-identified patent and that said Letters Patent is hereby corrected as shown below:

On the Title Page

On page 3, Column 2, item (56), other publications, Line 19, delete "ant -bacteriial" and insert -- anti-bacterial --, therefor.

On page 3, Column 2, item (56), other publications, Line 24, delete "iusing" and insert -- using --, therefor.

Signed and Sealed this
Sixteenth Day of March, 2021

Drew Hirshfeld
*Performing the Functions and Duties of the
Under Secretary of Commerce for Intellectual Property and
Director of the United States Patent and Trademark Office*